US012032735B2

(12) United States Patent
Rubin et al.

(10) Patent No.: US 12,032,735 B2
(45) Date of Patent: Jul. 9, 2024

(54) METHOD AND APPARATUS FOR REAL-TIME DATA COMMUNICATION IN FULL-PRESENCE IMMERSIVE PLATFORMS

(71) Applicant: Penumbra, Inc., Alameda, CA (US)

(72) Inventors: Amir Rubin, Los Gatos, CA (US); Joel Breton, Santa Rosa, CA (US); Ariel Z. Rubin, Los Angeles, CA (US); Scott C. Duensing, Smithton, IL (US); Alejandro S. Diaz, Ross, CA (US); William Herrera, Moreno Valley, CA (US); Christian Laursen, Phoenix, AZ (US); Andrew Yumul Huertas, Carson, CA (US); Danilo Moura Silva, Thousand Oaks, CA (US)

(73) Assignee: Penumbra, Inc., Alameda, CA (US)

( * ) Notice: Subject to any disclaimer, the term of this patent is extended or adjusted under 35 U.S.C. 154(b) by 165 days.

(21) Appl. No.: 17/844,416

(22) Filed: Jun. 20, 2022

(65) Prior Publication Data
US 2022/0407902 A1 Dec. 22, 2022

Related U.S. Application Data

(60) Provisional application No. 63/213,187, filed on Jun. 21, 2021.

(51) Int. Cl.
*G06F 3/01* (2006.01)
*G06F 3/14* (2006.01)
*G06T 19/00* (2011.01)
*H04L 65/1069* (2022.01)
*H04L 65/1089* (2022.01)
(Continued)

(52) U.S. Cl.
CPC ............. *G06F 3/012* (2013.01); *G06F 3/14* (2013.01); *G06T 19/00* (2013.01); *H04L 65/1069* (2013.01); *H04L 65/1089* (2013.01); *H04L 65/1093* (2013.01); *H04L 65/403* (2013.01);
(Continued)

(58) Field of Classification Search
None
See application file for complete search history.

(56) References Cited

U.S. PATENT DOCUMENTS 9,294,873 B1 * 3/2016 MacGregor ........... H04W 4/026
10,127,632 B1 11/2018 Burke et al.
(Continued)

OTHER PUBLICATIONS

U.S. Appl. No. 17/844,426, filed Jun. 20, 2022, Amir Rubin.

*Primary Examiner* — Talha M Nawaz
(74) *Attorney, Agent, or Firm* — HALEY GUILIANO LLP

(57) ABSTRACT

Real-time two-way communication between a user immersed in a virtual reality (VR) environment and another party who is not in the VR environment. The sequence of video frames being presented to the VR user on, e.g., a head mounted display, i.e., the VR user's "field of view" in the VR environment, is shown to a guest user on their computing device. Simultaneously, video from a camera in a guest user computing device is shown to the VR user in a window in the VR environment. Audio is also exchanged in real time between the VR user and guest user by use of a microphone and loudspeaker in both the VR system and the guest user computing device. The VR user's system can also support both rotational and translational user movement thus properly changing the VR user's apparent distance from objects displayed in the VR environment.

15 Claims, 15 Drawing Sheets

(51) Int. Cl.
*H04L 65/1093* (2022.01)
*H04L 65/403* (2022.01)
*H04N 7/15* (2006.01)

(52) U.S. Cl.
CPC ....... *H04N 7/152* (2013.01); *G06T 2219/024* (2013.01)

(56) References Cited

U.S. PATENT DOCUMENTS

| | | |
|---|---|---|
| 2013/0342572 A1 | 12/2013 | Poulos et al. |
| 2015/0205106 A1* | 7/2015 | Norden .............. G02B 27/0093 345/7 |
| 2016/0350973 A1* | 12/2016 | Shapira ................... G06F 3/011 |
| 2017/0256096 A1* | 9/2017 | Faaborg ................ G06T 19/003 |
| 2017/0287215 A1* | 10/2017 | Lalonde ................. G06F 3/012 |
| 2017/0339372 A1* | 11/2017 | Valli ...................... G06T 15/005 |
| 2018/0101990 A1* | 4/2018 | Yang ....................... G06T 13/40 |
| 2019/0056848 A1 | 2/2019 | Diverdi et al. |
| 2022/0404907 A1 | 12/2022 | Rubin et al. |

\* cited by examiner

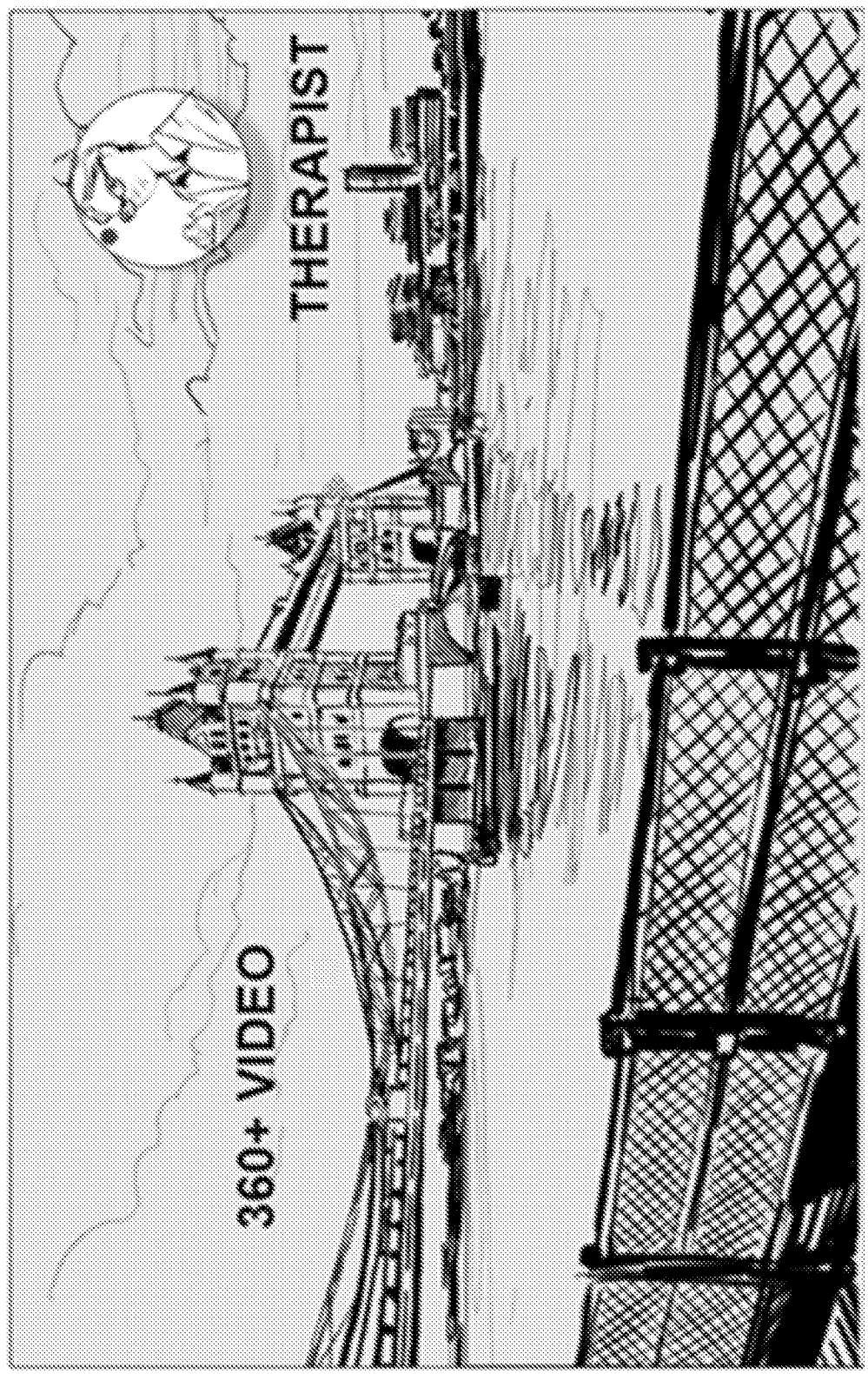

METHOD AND APPARATUS FOR REAL-TIME DATA COMMUNICATION IN FULL-PRESENCE IMMERSIVE PLATFORMS

This application claims priority to Provisional Application No. 63/213,187, filed Jun. 21, 2021, which is incorporated by reference herein in its entirety.

FIELD OF THE INVENTION

The present invention relates generally to virtual reality systems, and more particularly to the ability of a user of a virtual reality system to communicate and share the virtual reality experience with others while the user is in the virtual reality space.

BACKGROUND OF THE INVENTION

Remote real-time two-way communication of various kinds have advanced from systems that allowed only audio communication, such as radio or telephones, to systems that provide both audio and video communication, such as videoconference systems. Such videoconferences, otherwise known as teleconferences, have become common, and are easily conducted between, for example, computing devices, including mobile devices, such as tablet devices and smartphones, that have microphones, speakers, displays, and cameras, so that audio and video can be captured from a user on one such device, transmitted to another device in real-time (the transmission delays can be small enough to be unnoticeable), and reproduced for the user of the other device.

Different considerations apply to the evolving field of virtual reality. Virtual reality (VR) is often used to describe a wide variety of applications commonly associated with immersive, highly visual, computer-simulated environments that can simulate a user's physical presence in places in the real world or imagined worlds. While virtual reality can recreate a number of sensory experiences, the senses most commonly used today to create virtual reality appear to be sight and sound.

One method of presenting a virtual world to a user that is commonly identified with VR and presently in use is through the use of a headset, visor or helmet containing a video display which encompasses part or all of a user's field of view and presents computer generated images representing the VR environment, or "virtual world," to the user. Such a device is often referred to as a head-mounted display, or HMD.

By its nature, the HMD covers the user's eyes so that the user sees only the virtual world while wearing the HMD and the user is thus unable to see the actual physical world while in the virtual world. The user thus cannot have eye-to-eye contact with others, even if those others are in the same physical location and/or sharing the same virtual space.

Some existing VR social platforms enable physically remote users to interact within a virtual reality environment through audio or by creating cartoon 3D avatars to represent the other users inside a user's virtual environment. However, such systems are unable to fully replicate the experience of in-person interactions. Avatar systems often trigger a phenomenon known as the "uncanny valley," a common unsettling feeling people experience when androids (i.e., humanoid robots) and audio/visual simulations closely resemble humans in many respects but are not quite convincingly realistic.

Further, while a user wearing a HMD may receive audio from another party (either through the VR system or because the other party is physically present), the user is able to see only the VR environment presented by the HMD. These limitations hinder real-time two-way communication between a user in the VR environment and another party.

In various applications it is desirable to be able to allow a user immersed in a VR environment to communicate and interact with parties other than the VR user in real time, allow such other parties to view the portion of the VR environment that is within the user's field of vision, and allow the user to have eye-to-eye contact with the other parties, or view video supplied by other parties while the user is in the virtual reality environment.

Another issue is that conventional VR environments only allow the virtual reality user to see the effect of their movement with three degrees of freedom; thus, the VR user can move their head to change the orientation of the HMD rotationally around three different axes to see a different field of view of the virtual reality environment. However, changing position by the VR user in the real world, i.e., translational movement, requiring six degrees of freedom, by the VR user has no effect; for example, moving in what appears to be a direction toward a virtual object, does not change the apparent size of the virtual object. This can have a disconcerting effect on the VR user.

In some applications it is desirable to simulate six degrees of freedom of motion of the VR user to provide a more realistic VR experience.

SUMMARY OF THE INVENTION

A system and method is disclosed which allows a user immersed in a virtual reality environment to communicate and interact with other parties in real time, and allows such other parties to view at least a portion of the VR environment that is within the user's field of vision. A system and method is also disclosed for a VR user to experience six degrees of freedom of movement in the virtual reality environment.

One embodiment discloses a method of providing real-time, two-way communication between a virtual reality user, viewing on a virtual reality display device a displayed sequence of video frames comprising the virtual reality user's field of view of a virtual reality environment, and a guest user operating a computing device having a camera and microphone, comprising: creating, by a processor, a connection between the virtual reality display device and the computing device of the guest user; capturing, by the processor, the sequence of video frames displayed to the virtual reality user on the virtual reality display device; generating, by a microphone, an audio signal from the virtual reality user; sending, by the processor, the captured sequence of video frames displayed to the virtual reality user and the generated audio signal from the virtual reality user to the computing device of the guest user; displaying, by the computing device of the guest user, the captured sequence of video frames; playing, by the computing device of the guest user, the generated audio signal from the virtual reality user; capturing, by the camera of the computing device of the guest user, a video stream of the guest user; generating, by the microphone of the computing device of the guest user, an audio signal from the guest user; sending, by the computing device of the guest user, the captured video stream of the guest user and the generated audio signal from the guest user to the processor; displaying, by the processor, the captured video stream of the guest user in a window in the virtual reality environment; and playing, by the processor, the generated audio signal from the guest user.

Another embodiment discloses a system for providing real-time two-way communication between a virtual reality user, and a guest user operating a computing device containing a camera and microphone, comprising: a virtual reality display device configured to display a sequence of video frames comprising the virtual reality user's field of view of a virtual reality environment; a microphone configured to generate a first audio signal from the virtual reality user; a processor configured to: create a connection between the virtual reality display device and the computing device of the guest user; capture the sequence of video frames displayed to the virtual reality user on the virtual reality display device; send the captured sequence of frames displayed to the virtual reality user and the first audio signal to the computing device of the guest user; receive a video stream and a second audio signal from the computing device of the guest user; display the video stream from the computing device of the guest user in a window in the virtual reality environment; and a transducer configured to play the second audio signal.

Still another embodiment discloses a non-transitory computer readable storage medium having embodied thereon instructions for causing a computing device to execute a method for providing real-time, two-way communication between a virtual reality user, viewing on a virtual reality display device a displayed sequence of video frames comprising the virtual reality user's field of view of a virtual reality environment, and a guest user operating a computing device having a camera and microphone, the method comprising: creating, by a processor, a connection between the virtual reality display device and the computing device of the guest user; capturing, by the processor, the sequence of video frames displayed to the virtual reality user on the virtual reality display device; generating, by a microphone, an audio signal from the virtual reality user; sending, by the processor, the captured sequence of video frames displayed to the virtual reality user and the generated audio signal from the virtual reality user to the computing device of the guest user; displaying, by the computing device of the guest user, the captured sequence of video frames; playing, by the computing device of the guest user, the generated audio signal from the virtual reality user; capturing, by the camera of the computing device of the guest user, a video stream of the guest user; generating, by the microphone of the computing device of the guest user, an audio signal from the guest user; sending, by the computing device of the guest user, the captured video stream of the guest user and the generated audio signal from the guest user to the processor; displaying, by the processor, the captured video stream of the guest user in a window in the virtual reality environment; and playing, by the processor, the generated audio signal from the guest user.

Yet another embodiment discloses a method for a user wearing a head-mounted display (HMD) to experience movement with six degrees of freedom in a virtual reality environment, the HMD covering the user's field of vision and having a HMD tracker which provides information regarding the position and orientation of the HMD, comprising: determining, by a processor, an initial position and orientation of the user using information from the HMD tracker; generating, by the processor, a three-dimensional virtual reality environment configured as a sphere of a predefined radius around the user with three-dimensional virtual objects located on the surface of the sphere, each virtual object having an initial apparent depth from the determined initial position and orientation of the user; generating and outputting, by the processor, instructions to the HMD to display a portion of the virtual reality environment that is within the user's field of view based upon the determined initial position and orientation of the HMD; determining, by the processor, using information from the HMD tracker that the user has moved rotationally; generating and outputting, by the processor, instructions to the HMD to display a different portion of the virtual reality environment that is within the user's field of view after the user's rotational movement relative to the sphere; determining, by the processor, using information from the HMD tracker that the user has moved translationally; and generating and outputting, by the processor, instructions to the HMD to display a different portion of the virtual reality environment that is within the user's field of view after the user's translational movement relative to the sphere and to display any virtual objects within the user's field of view at a new apparent position and depth corresponding to the user's translational movement relative to the sphere.

Still another embodiment discloses a system for a user to experience movement with six degrees of freedom in a virtual reality environment, comprising: a head-mounted display (HMD) covering the user's field of vision and having a HMD tracker which provides information regarding the position and orientation of the HMD; a processor configured to: determine an initial position and orientation of the user using information from the HMD tracker; generate a three-dimensional virtual reality environment configured as a sphere of a predefined radius around the user with three-dimensional virtual objects located on the surface of the sphere, each virtual object having an initial apparent depth from the determined initial position and orientation of the user; generate and output instructions to the HMD to display a portion of the virtual reality environment that is within the user's field of view based upon the determined initial position and orientation of the user's head; determine using information from the HMD tracker that the user has moved rotationally; generate and output instructions to the HMD to display a different portion of the virtual reality environment that is within the user's field of view after the user's rotational movement relative to the sphere; determine using information from HMD the tracker that the user has moved translationally; generate and output instructions to the HMD to display a different portion of the virtual reality environment that is within the user's field of view after the user's translational movement relative to the sphere and to display any virtual objects within the user's field of view at a new apparent position and depth corresponding to the user's translational movement relative to the sphere.

Yet another embodiment discloses a non-transitory computer readable storage medium having embodied thereon instructions for causing a computing device to execute a method for a user wearing a head-mounted display (HMD) to experience movement with six degrees of freedom in a virtual reality environment, the HMD covering the user's field of vision and having a HMD tracker which provides information regarding the position and orientation of the HMD, the method comprising: determining, by a processor, an initial position and orientation of the user using information from the HMD tracker; generating, by the processor, a three-dimensional virtual reality environment configured as a sphere of a predefined radius around the user with three-dimensional virtual objects located on the surface of the sphere, each virtual object having an initial apparent depth from the determined initial position and orientation of the user; generating and outputting, by the processor, instructions to the HMD to display a portion of the virtual reality environment that is within the user's field of view based upon the determined initial position and orientation of the HMD; determining, by the processor, using information from the HMD tracker that the user has moved rotationally; generating and outputting, by the processor, instructions to the HMD to display a different portion of the virtual reality environment that is within the user's field of view after the user's rotational movement relative to the sphere; and determining, by the processor, using information from the HMD tracker that the user has moved translationally; generating and outputting, by the processor, instructions to the HMD to display a different portion of the virtual reality environment that is within the user's field of view after the user's translational movement relative to the sphere and to display any virtual objects within the user's field of view at a new apparent position and depth corresponding to the user's translational movement relative to the sphere.

BRIEF DESCRIPTION OF THE DRAWINGS

FIG. 16 shows a virtual reality environment displayed to a therapy patient, operating as a virtual reality user, in a HMD in one embodiment of the present approach.

DETAILED DESCRIPTION OF THE INVENTION

A system and method is disclosed for a user immersed in a virtual reality (hereinafter described as a "VR user") to communicate and interact with one or more parties other than the VR user (hereinafter "guest users"), and for such a guest user to view at least a portion of the virtual reality that is within the VR user's field of vision. In addition, two VR users may communicate with each other without being limited to viewing each other merely as cartoon avatars.

A system and method is also disclosed for a VR user to experience six degrees of freedom of movement in the virtual reality environment.

VR display devices such as a HMD typically work by presenting a VR user with a sequence of video frames showing what is in the VR environment in a particular direction in which the VR user is "looking," i.e., the direction in which the front of the HMD, and thus the VR user's head, is oriented. In the present approach, the video frames being presented to the VR user, i.e., the VR user's "view" of the VR environment, is displayed on a computing device of the guest user such as a desktop or laptop computer, smartphone, or tablet.

Simultaneously, video from a camera built into or connected to the guest user computing device, which is typically, but not limited to, video of the guest user, is displayed to the VR user in a window that appears in the VR user's display (e.g., the VR user's HMD). Audio is exchanged between the VR user and guest user by use of a microphone and speaker or other transducer in both the VR system and the guest user computing devices. In this way, real-time two-way communication between a VR user and a guest user who is not in a VR environment is accomplished.

As used herein, virtual reality (VR) refers to a completely virtual, digital environment in which the VR user is fully immersed. Typically the VR user will have no visual sense of the real, or physical, world and, in some embodiments, will also only receive audio through a speaker or earbud and thus have no audio sense of the real world. While the below discussion refers to VR, one of skill in the art will appreciate that the techniques described herein may also be applied to "augmented reality" (AR), in which a user perceives the real world with an overlay of digital information, and "mixed reality" (MR), in which the real world and a virtual reality are intertwined, and the user may interact with both physical objects in the real world and digital objects in the virtual reality.

Figure 1:
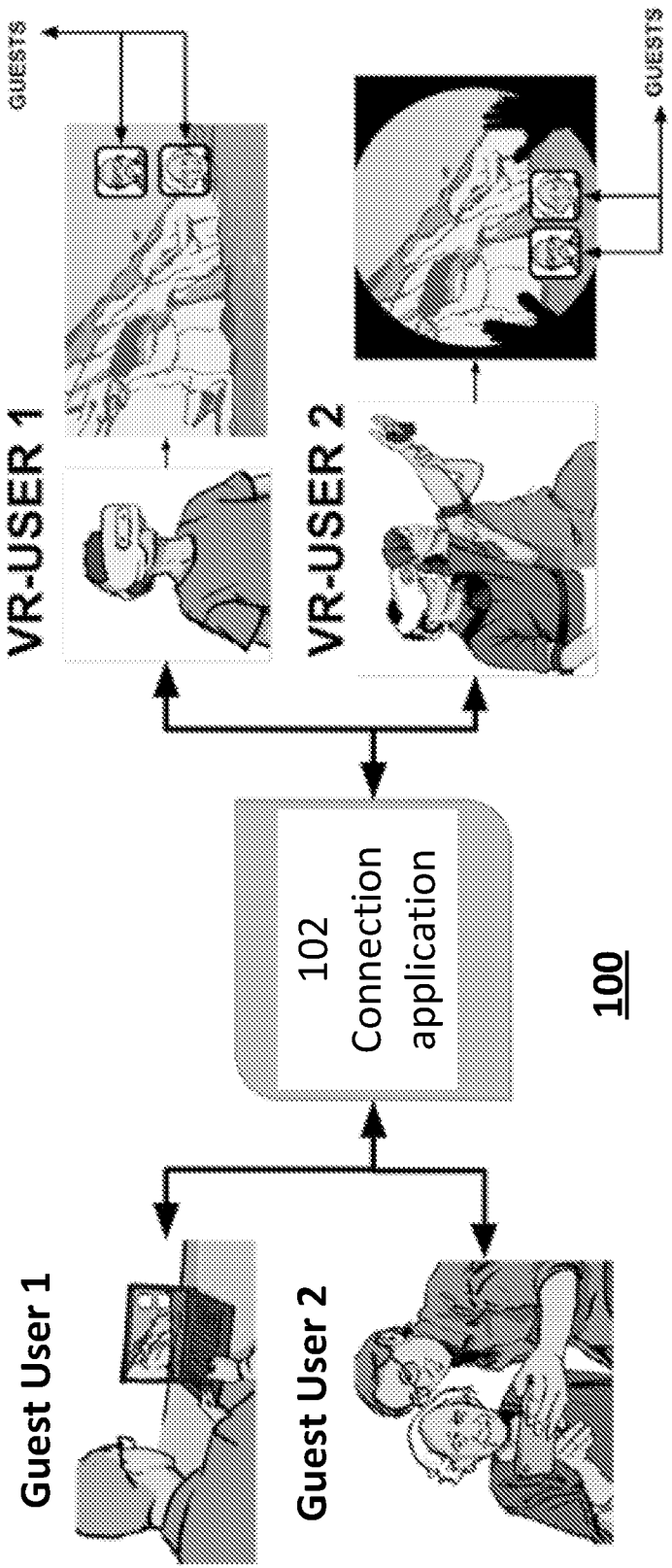
FIG. 1 is a simplified diagram showing the operation of a system for one or more virtual reality users immersed in a virtual reality environment to communicate and interact with guest users according to one embodiment of the present approach.

FIG. 1 is a simplified diagram showing the operation of a system 100 for two-way real-time audio and video communication between one or more VR users immersed in a VR environment and one or more guest users according to one embodiment of the present approach.

Such communication involves one or more VR users and one or more guest users. While, as discussed below, a simple configuration involves a single VR user and a single guest user, the technique of the present application may be applied to multiple VR users and multiple guest users. FIG. 1 illustrates an example of two VR users, VR-User 1 and VR-User 2, and two guest users, Guest User 1 and Guest User 2 but the present approach is intended to support any number and combination of VR users and guest users.

Consider the simple configuration of the first VR user, VR-User 1, and the first guest user, Guest User 1. VR-User 1 is shown wearing a HMD and viewing a VR environment, while Guest User 1 is shown using a laptop computer. A connection application 102 connects VR-User 1 to Guest User 1 for the two-way real-time communication by transmitting audio and video between them. The portion of the VR environment being displayed to VR-User 1 on the HMD is simultaneously being shown to Guest User 1 on the laptop.

As shown in FIG. 1, a small window in the VR environment displayed to VR-User 1 by the HMD contains a feed from the camera in or connected to the laptop being used by Guest User 1, and thus in this case shows video of Guest User 1 to VR-User 1, assuming that the camera is pointed at Guest User 1 (a guest user could choose to point the camera somewhere else). VR-User 1 also has a microphone and one or more speakers or earpieces (typically contained in the HMD), while the laptop used by Guest User 1 has a microphone and one or more speakers, and thus VR-User 1 and Guest User 1 can talk to each other in real time.

As also shown in FIG. 1, a similar situation applies between VR-User 1 and Guest User 2, except that Guest User 2 is using a smartphone or tablet (essentially any handheld device). Again, the portion of the VR environment being displayed to VR-User 1 on the HMD is simultaneously being shown to Guest User 2 on the smartphone or tablet (the screen of the smartphone or tablet is not shown here), a small window in the VR environment shows video from the smartphone or tablet of Guest User 2 to VR-User 1, and VR-User 1 and Guest User 2 are able to talk to each other in real time through their respective microphones and speakers. (As shown in FIG. 1, a "guest user" may actually be more than one person participating via a single device.)

FIG. 1 also illustrates a second VR user, VR-User 2, sharing the VR environment with VR-User 1. As with VR-User 1, guest windows are presented on the display of VR-User 2 showing Guest User 1 and Guest User 2. VR-User 2 also has the ability to communicate by audio with VR-User 1, Guest User 1 and Guest User 2. In this illustration, both VR-User 1 and VR-User 2 are sharing their virtual immersive experience with Guest User 1 and Guest User 2.

As shown in FIG. 1, the view of the VR environment displayed to VR-User 2 is substantially similar to that displayed to VR-User 1, and thus only one view of the VR environment need be displayed to each of the guest users. However, it will be appreciated that separate feeds from the HMDs of VR-User 1 and VR-User 2 may be displayed to a guest user simultaneously, for example, by the use of a split screen or windowing technique.

While not shown in FIG. 1, in addition to the video feed from the HMD of a VR user, it will also be appreciated that each guest user, in addition to seeing the VR feed from a HMD, may also see small windows displayed within the VR feed in the same fashion that a VR user sees small windows displayed within the VR feed on the HMD. For example, Guest User 1 may see a display of one small window containing the view from his own camera, i.e., a picture of himself as is not uncommon in videoconferencing applications, and a display of another small window containing the video feed from Guest User 2. In general, all of the users will share an audio connection, so that Guest User 1 and Guest User 2 will also be able to talk to each other directly as well as talking to VR-User 1 and VR-User 2, but communication between certain users may be limited if desired.

As above, video conferencing between users, such as Guest User 1 and Guest User 2, is well known, as is allowing VR users, such as VR-user 1 and VR-user 2, to share a virtual reality environment in which each VR user sees the other as a cartoon avatar. However, the real-time two-way communication between one or more VR user and one or more guest user of the present approach is novel.

Figure 2:
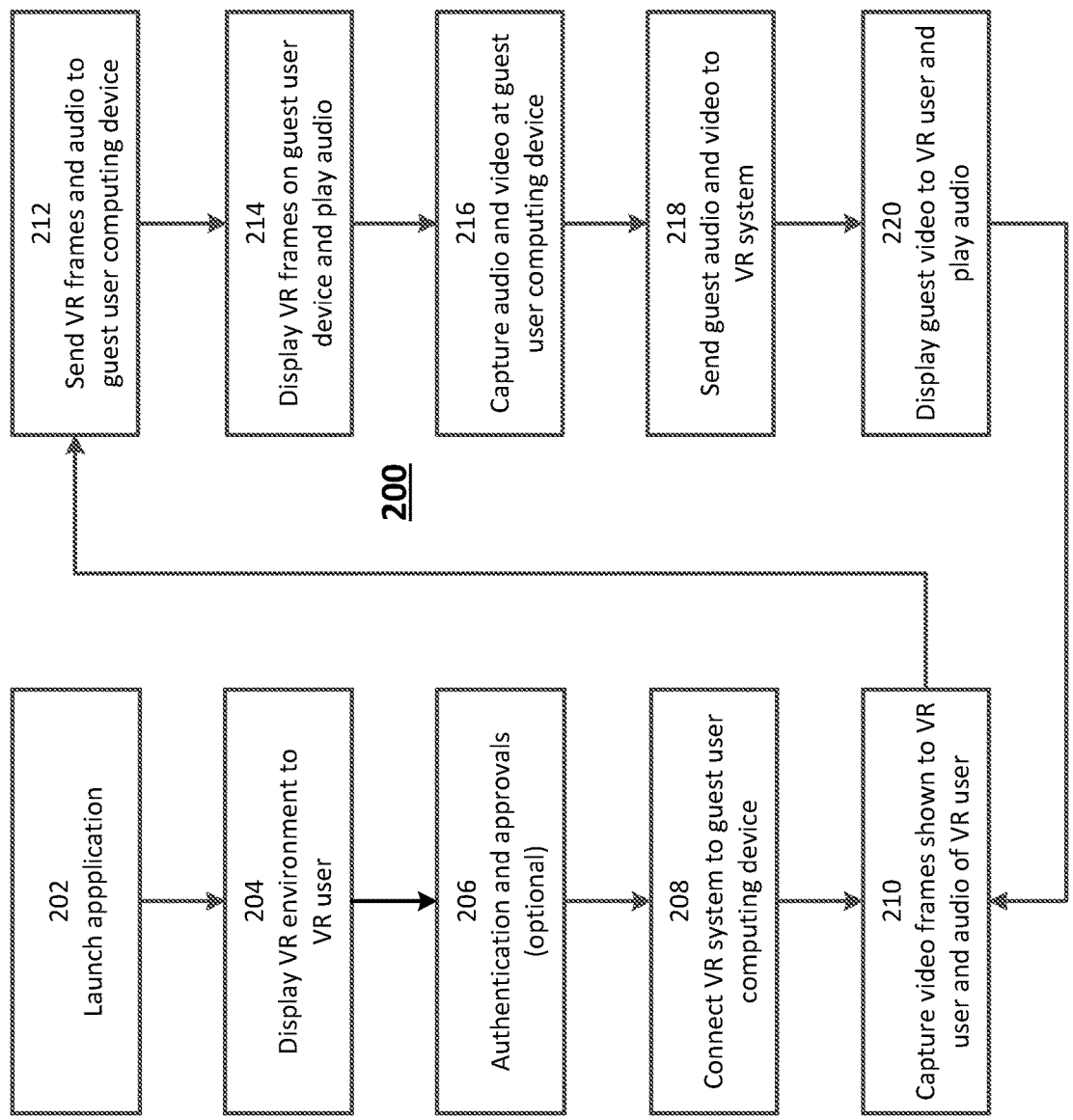
FIG. 2 is a flowchart of a method for a VR user to communicate and interact with a guest user according to one embodiment of the present approach.

FIG. 2 is a flowchart of a method 200 for a VR user to communicate and interact with a guest user according to one embodiment of the present approach.

At step 202, the application that connects and facilitates communication between a VR user and a guest user is launched. At step 204, a VR system having a display device (e.g., a HMD) displays a VR environment to the VR user.

At optional step 206, various authentication and approval steps may take place. For example, where the VR system and guest user computing device are remote from each other, some form of identification may be required for each to identify the other using the connection application. This may be similar to the way in which video conferences currently authenticate participants, for example, requiring an identification number or user identification, clicking on a link that has been provided, etc. For security and/or privacy purposes, the present approach can require approvals from each party to proceed, so that the VR user must approve sharing audio and video from the VR system with the guest user, and the guest user must approve sharing audio and video from their computing device with the VR user.

At step 208, the VR system is communicatively connected to the guest user computing device. The connection may be direct if, for example, the VR system and the guest user computing device are in the same physical location. Alternatively, if the VR system and guest user computing device are remote from each other, the connection may be made over a network such as the internet through a server running the connection application.

At step 210, video frames of the VR environment that are being displayed on the HMD to the VR user are captured. As will be discussed below, the VR environment may be a three-dimensional environment that virtually surrounds the VR user, and the VR user is free to look in any direction, but there will be a specific field of view of the user in that direction displayed on, for example, the HMD, and thus only that part of the VR environment will be seen by the VR user. Thus, capturing the frames that are actually shown to the VR user will capture that part of the VR environment that is being displayed to the VR user, and not some other portion of the VR environment. Audio from the VR user is also captured by a microphone, as was discussed above.

At step 212, the captured VR frames and VR user audio are sent to the guest user computing device, and at step 214 are displayed on and output from the guest user computing device. Since as above the VR frames are the same ones displayed to the VR user, the guest user sees the same portion of the VR environment that the VR user does, but cannot look elsewhere in the VR environment unless the VR user does so.

At step 216, the guest user computing device captures audio and video in its vicinity. As above, for two-way communication it is assumed that in general the camera of the guest user computing device will be pointed at the guest user, and the microphone will pick up the voice of the guest user, but this need not be the case if some other input is desired.

At step 218, the audio and video captured by the guest user computing device is sent to the VR system via the communication application, and, at step 220, displayed on and output from the VR user's device (e.g., the HMD) to the VR user. As discussed above, the video from the guest user computing device will typically be displayed in a small window in the VR environment displayed on the VR user's device (e.g., the HMD), and the audio played to the VR user through, for example, one or more speakers or earpieces of the VR user (e.g., the HMD).

The process then returns to step 210 for the capture of more VR video frames and audio from the VR user and repeats steps 210 to 220 until the connection is terminated. Stated differently, to support the two-way real-time communication between a VR user and a guest user, steps 210 through 220 can all be happening simultaneously. For example, displaying guest user video to a VR user in step 220 can be happening at the same point in time as capturing video frames displayed to a VR user in step 210.

It will be apparent to one of skill in the art that additional VR users or guest users, as shown in FIG. 1 above, may be treated in the same fashion. The video frames displayed to VR-User 1 and the audio captured from VR-User 1 may be shared with multiple guest users, and more than one guest user window may be shown in the VR environment displayed to VR-User 1. Similarly, the captured audio from, VR-User 2 may be shared with one or more guest users in the same way as that from VR-User 1, and one or more windows of captured video from guest users shown in the VR environment displayed to VR-User 2. As above, even the video frames shown to VR-User 2 may be shared with guest users, which may of particular interest if VR-User 2 is viewing a different portion of the VR environment, accessing different virtual controllers or objects, or viewing their own avatar (such as virtual hands).

It will also be appreciated by one of skill in the art that a high frame rate is required to render a VR environment in a way that does not create discomfort, and even motion sickness, in the VR user. The transmission of these frames to a guest user computing device may require significant processing power and bandwidth. For this reason, in some embodiments, not all of the frames shown to the VR user are sent to the guest user computing device. In these embodiments, rather than copying all of the frames displayed to the VR user, not all frames or only parts of each frame are copied in intervals to reduce the processing time that would be necessary to copy the entire frame.

The frequency of copying the frames may be defined based upon the processing speed available to have the frames ready for streaming to the guest user computing device. For example, if the VR system runs at 60 frames per second, a "frame skip" of five would result in 12 frames per second being sent to a guest user.

Further, in some embodiments, the resolution of render texture of the frames shown to the VR user may be reduced. The frame skip and the amount of render texture copied may be modified to reduce the number of pixels that need to be copied and achieve a balance between the VR system frame rate and the video stream frame rate refresh for guest users.

Figure 3:
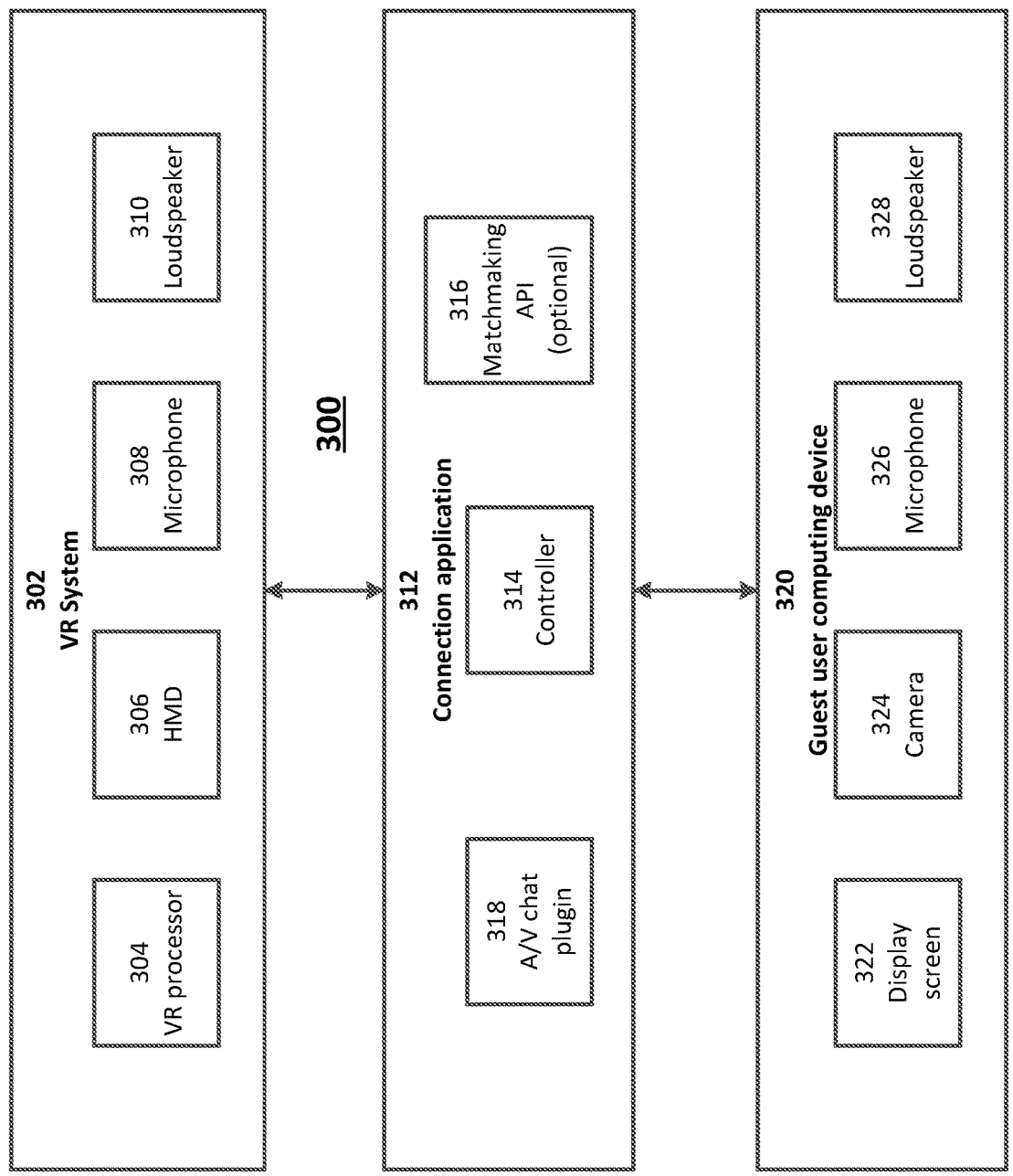
FIG. 3 is a block diagram of a system for real-time two-way communication between a VR user and a guest user according to one embodiment of the present approach.

FIG. 3 is a block diagram of a system 300 for real-time two-way audio and video communication between one or more VR user and one or more guest user according to one embodiment of the present approach.

A VR system 302 displays a VR environment to a VR user. VR system 302 contains a VR processor 304 which generates the VR environment. A HMD 306 worn by the VR user displays a portion of the VR environment to the VR user; HMD 306 typically has a controller, such as a magnetic tracker, that provides information from which the VR processor can determine the position and orientation of the HMD 306, and thus the position and orientation of the VR user's head, and the VR processor 304 can thus determine the portion of the VR environment to display (i.e., the field of vision of the VR user within the VR environment). (One of skill in the art will appreciate that there are other ways of determining the position and orientation of a HMD of a user.)

As above, in a typical VR environment, HMD 306 displays a portion of the VR environment that is a field of vision of the VR user that does not allow the VR user to see the entire VR environment at once, but rather only what is in the VR user's field of vision. Thus, the VR user can control which part of the VR environment is to be displayed for them to see by moving their head, and thus HMD 306, thereby effectively looking in various directions. VR processor 304 displays on HMD 306 the portion of the VR environment that corresponds to the field of vision in the direction that the HMD is pointed.

A microphone 308 captures audio from the VR user that may be used for various purposes; there may be voice commands in some applications, the VR user may wish to communicate with other players in a game in the VR environment, or the VR user may desire to have real-time communication with a guest user as described herein. A loudspeaker 310 (or other transducer, such as an earbud or headphone) provides sound to the VR user. Again, the sound may be from an application, may be other players in a game, or may be part of real-time communication with a guest user.

It is to be noted that while VR system 302 is described here as itself containing VR processor 304, HMD 306, microphone 308 and loudspeaker 310, it is to be understood that HMD 306 may itself operate as VR system 302 by itself containing one or more of the other elements shown and described. Similarly, while the example described is a HMD, other known virtual reality devices can likewise be used in another embodiment of the present approach.

In the present approach, a guest user uses a computing device 320, such as a desktop or laptop computer, a smartphone, or a computing tablet. As is typical, guest user computing device 320 contains a display screen 322 for displaying pictures and video, a camera 324 that is able to capture pictures and video of the user of the computing device, a microphone 326 for capturing audio from the device user, and a loudspeaker or other transducer 328 for producing sound to the computing device user. As above, it is currently common for users to use such computing devices to participate in video conferences, in which the device user can see and hear other participants and be seen and heard by those other participants.

A connection application 312 connects the VR system and the guest user computing device 310. Connection application 312 contains a controller 314 that coordinates the connection between VR system 302 and guest user computing device 320, an audio/video chat plugin that is able to pass audio and video from VR system 302 and guest user computing device 320 in both directions, and an optional matchmaking API that allows for identification of a specific VR system 302 and guest user computing device that are to be connected, authorization from a VR user and guest user to connect to each other, and similar matchmaking functions.

These components facilitate the video frames displayed on a HMD of a VR user to be communicated for display to a guest user computing device, for video from the guest user computing device camera to be communicated for display in a window in the VR environment displayed on the HMD of the VR user, and audio to be exchanged between the VR user and a guest user, thus facilitating real-time two-way audio and video communication.

Having described a system and method for facilitating real-time two-way audio and video communication between a VR user and a guest user, another common issue in VR systems is that VR displays are generally not sensitive to, or do not properly handle, translational movement by the VR user. Described herein is an approach that helps to address this issue by allowing a VR user's movements to change the VR user's apparent distance from objects displayed in the VR environment.

Figure 4:
FIG. 4 illustrates how views may be taken from multiple cameras, each camera capturing a slightly different view of a subject area according to the prior art.
Figure 5:
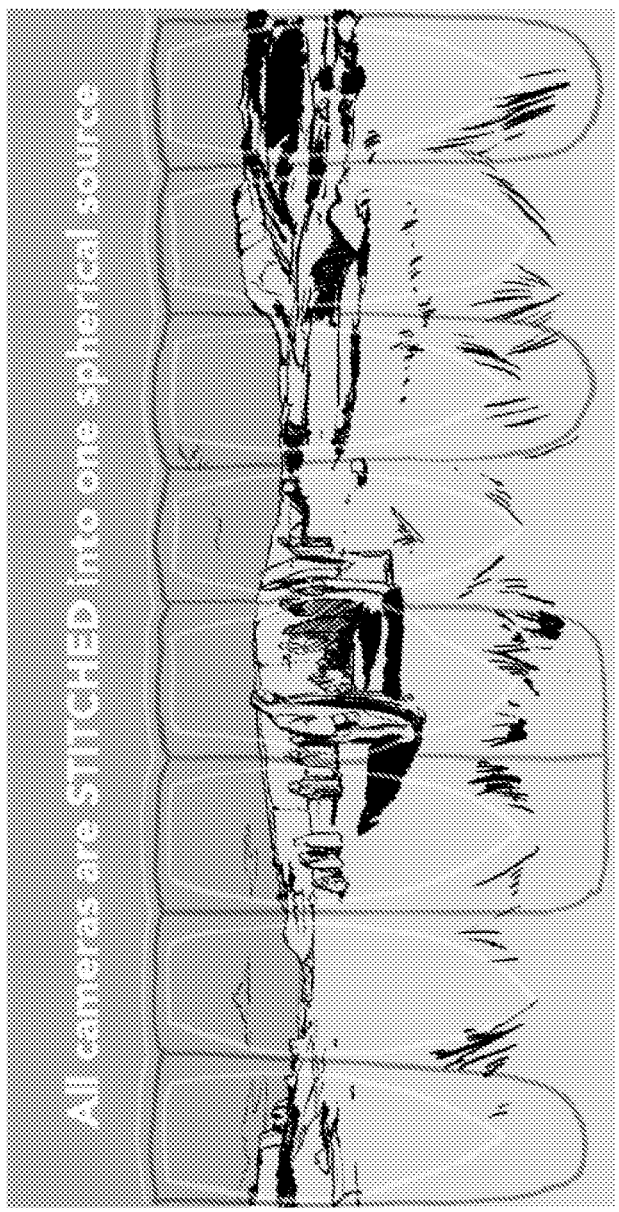
FIG. 5 illustrates how views from multiple cameras as shown in FIG. 6 may be stitched together to form a wider, continuous view of the subject area according to the prior art.

Immersive video, also known as 360-degree video or spherical video, is known in the art. Such video is created by taking video recordings from multiple cameras mounted closely together, so that a view in every direction is recorded at the same time, and then "stitching" the views together, i.e., placing the views in a row and adjusting the overlapping portions of the views to form a continuous image. FIGS. 4 and 5 illustrate how this is typically done.

FIG. 4 illustrates views from multiple cameras such as cameras A, B and C. Each camera captures a slightly different view of a subject area, in this illustration a landscape. The views from multiple cameras are then stitched together to form a wider, continuous view of the landscape.

FIG. 5 illustrates the result of views from multiple cameras, such as those shown in FIG. 4, being stitched together to construct a wider, continuous view of the subject area according to the prior art. In this example, there are eight views stitched together, with the stitch lines visible. As is known in the art, a 360-degree or spherical view may be constructed from a sufficient number of camera views in all directions.

Inside a spherical projection constructed in this way, a viewer has control of the viewing direction, much as one can choose where to look in a spherical panorama or planetarium. However, users watching such projections are traditionally placed in a static position in the center of the spherical projection and locked from any change of that position. This applies to the virtual position of a VR user as well.

The concept of "degrees of freedom" of movement, i.e., the ways in which an object, such as a user's head or a HMD worn by the user, may change its position and orientation, is well known in the art. A system may have different numbers of degrees of freedom, but the most common examples are three degrees of freedom, common referred to as 3DOF, and six degrees of freedom, or 6DOF, depending upon whether the object is in a fixed position and may only change its orientation, i.e., may only move rotationally, as is the case of 3DOF, or may also move in space, i.e., translationally, as is the case of 6DOF.

Figure 6:
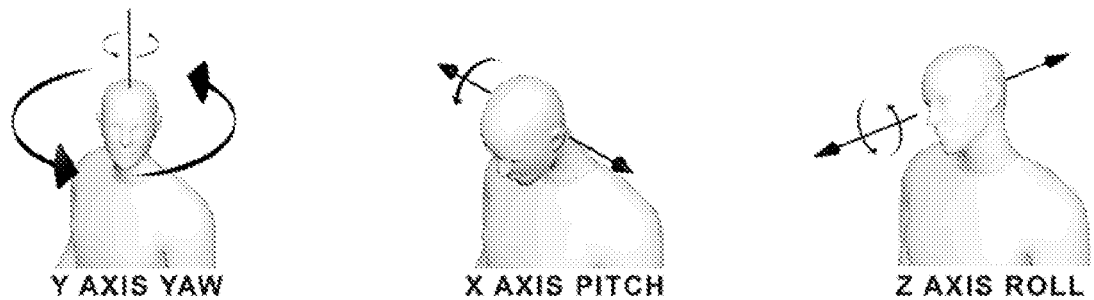
FIG. 6 illustrates how a person may move their head in a system having three degrees of freedom of movement as known in the prior art.

FIG. 6 illustrates how an object, here a user's head, may move if it is limited to 3DOF of movement. The head may rotate around each of the axes of three-dimensional space, i.e., the X, Y and Z axes as shown, and thus change its orientation, but does not change its position in space. Conventionally, these rotations are known as pitch, yaw and roll; pitch is the rotation of an object about the transverse axis, roll is the rotation of the object about the longitudinal axis, axed yaw is the rotation of the object about the vertical axis.

Figure 7:
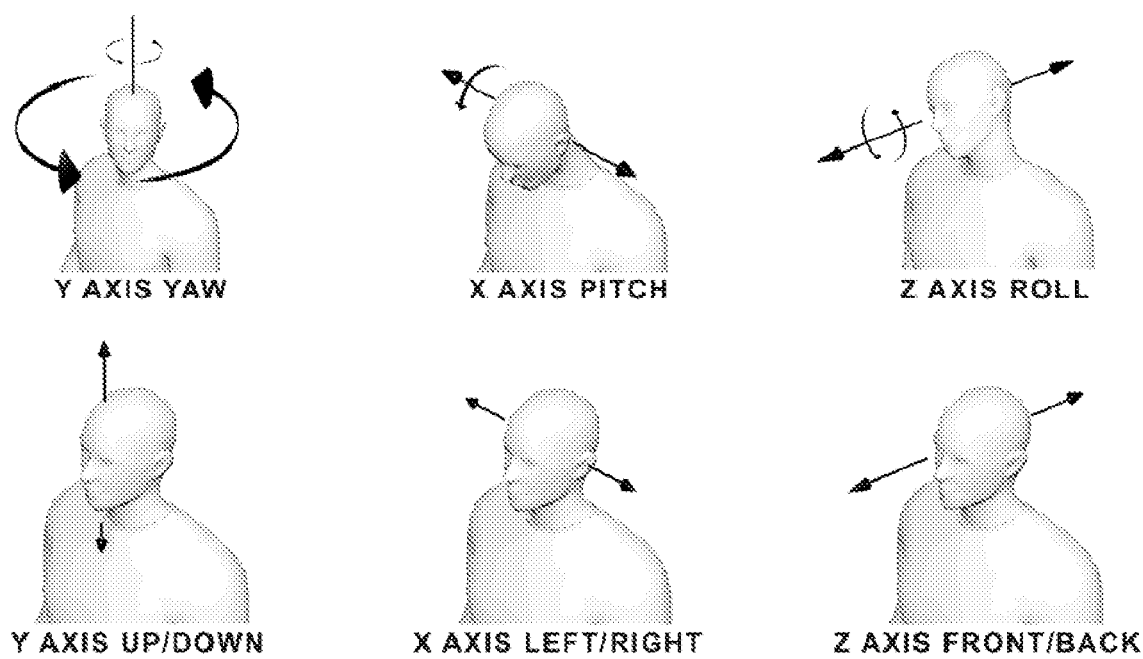
FIG. 7 illustrates how a person may move their head in a system having six degrees of freedom of movement as known in the prior art.

FIG. 7 illustrates how an object may move when 6DOF of movement are available. In addition to the change in orientation from the pitch, yaw and roll of a 3DOF system, the object (here a user's head) may also now move its position in space. The object may move vertically, i.e., up and down, or horizontally in either of two directions, i.e., front and back or left and right.

The difference in these motions is easily understood in the real world. If a person looks at an object and tilts their head sideways (i.e., a Z axis roll as shown in FIG. 6), the object is now in a slightly different place in the person's field of view, but the size of the object will not change. On the other hand, if a person moves their head closer to an object (i.e., a Z axis front movement as shown in FIG. 7), the object's apparent size will become larger.

In the prior art, a VR user wearing a HMD is limited to 3DOF; the VR user is able to rotate their head in any direction to see a different part of the spherical projection, but not to move "closer to" or "farther from" the projection. As with objects in the real world, the apparent size of objects in the VR user's field of view will not change.

Figure 8:
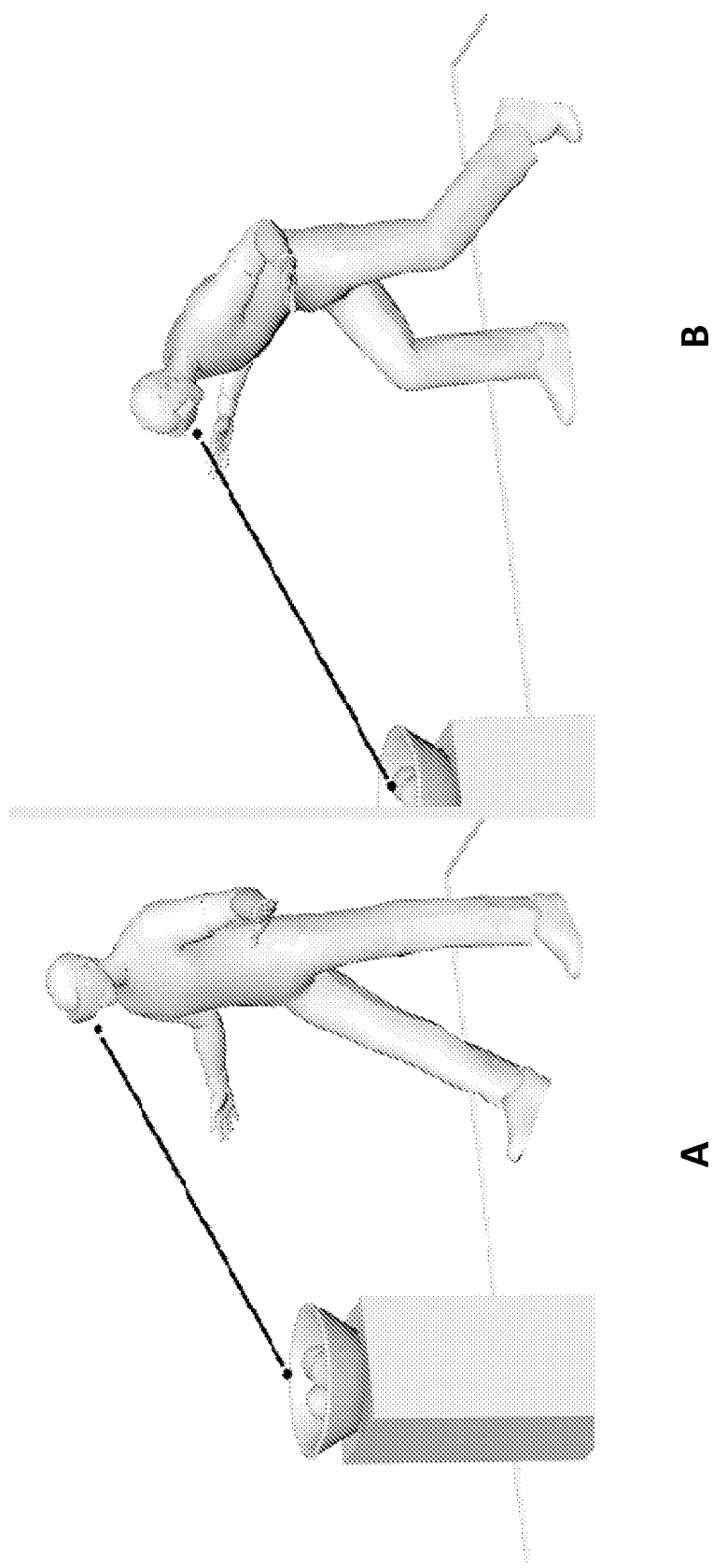
FIG. 8 illustrates the effect of a virtual reality user's attempt to approach a virtual object according to the prior art.

FIG. 8 illustrates the effect of a virtual reality user's attempt to approach a virtual object according to the prior art. In drawing A of FIG. 8, a VR user sees a virtual object (in this case a bowl of fruit) in the VR environment; the virtual object is at an apparent distance from the VR user as indicated by the double arrowhead line in the figure.

In drawing B of FIG. 8, the VR user has taken a physical step in the real world in the apparent direction of the virtual object. However, because the HMD of the prior art only provides 3DOF, the physical step has no effect on the VR projection as it is translational movement not recognized in a 3DOF system (again, the VR user is kept at a fixed position in the virtual space despite their actual translational movement). The virtual object remains at the same apparent distance from the VR user as indicated by the same length double arrowhead line in the figure. This can create confusion and discomfort, and even nausea, in the VR user as displayed objects in the virtual space thus do not move in a natural way, as there is no correspondence between movement in the real world and the VR environment.

Figure 9:
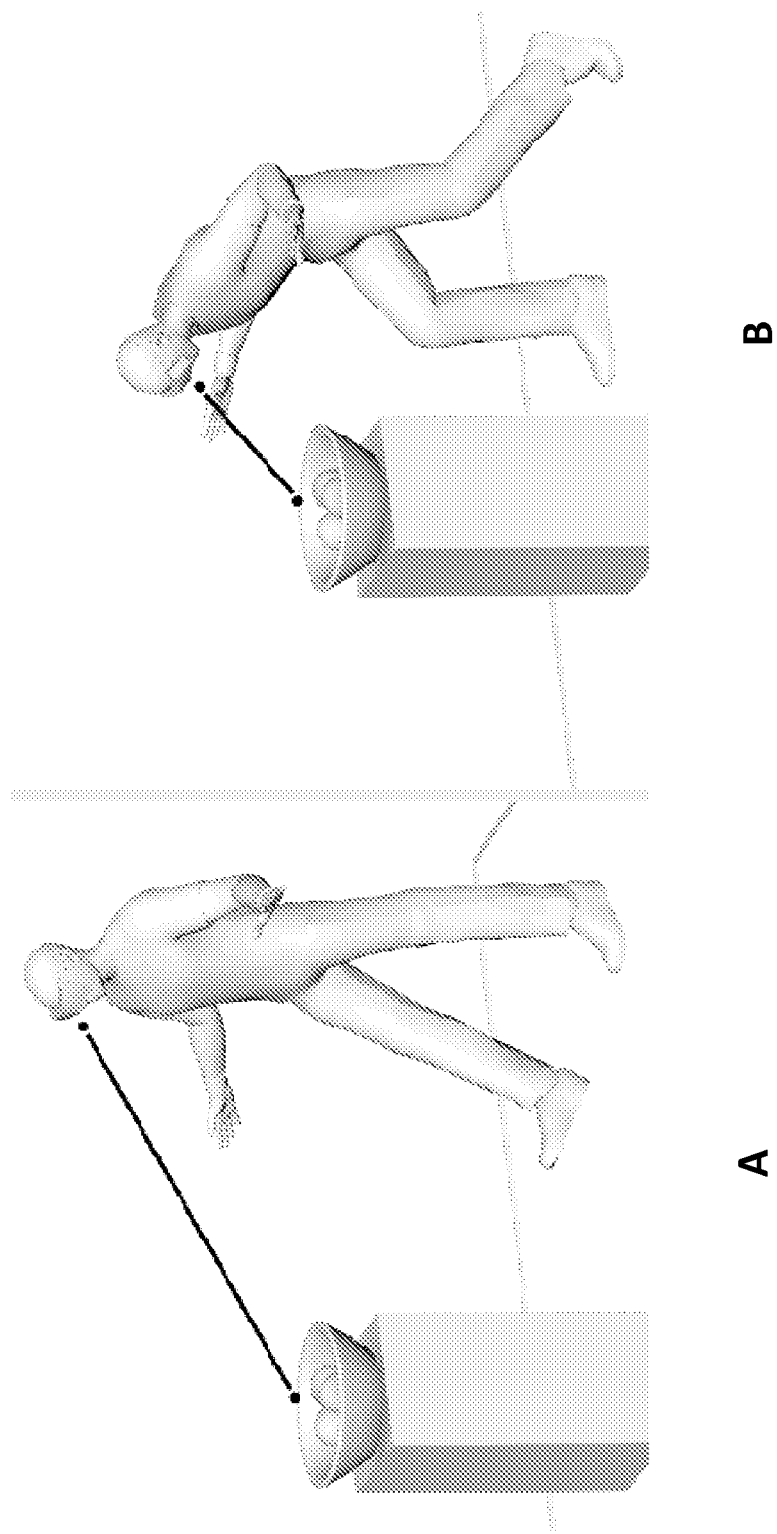
FIG. 9 illustrates the effect of a virtual reality user's attempt to approach a virtual object according to one embodiment of the present approach.

FIG. 9 illustrates the effect of a virtual reality user's translational movement towards a virtual object according to one embodiment of the present approach. Drawing A of FIG. 9 is the same as drawing A of FIG. 9; the VR user sees a virtual object in the VR environment at an apparent distance as again indicated by the double arrowhead line in the figure.

In drawing B of FIG. 9, the VR user has again taken a physical step (a translational movement) in the real world in the apparent direction of the virtual object. If the HMD has 6DOF and the virtual projection can adapt to the VR user's change in physical position due to the translational movement, then the VR user should see the virtual object at a smaller apparent distance (as shown by a shortened double arrowhead line in the figure), and the virtual object should appear larger. This will allow the VR user to perceive the VR environment more naturally, as there is now a correspondence between the VR user's movement in the real world and the apparent movement in the VR environment. However, conventional 360-degree videos cannot natively support such 6DOF movements, because there is no depth information in the video. Providing a "full presence immersive video" (FPIMV) system that can simulate 6DOF movement requires a different technique than the conventional 360-degree videos described above.

It is to be noted that known systems support translational movement by instead connecting multiple 360-degree videos. In this way, a VR user can move from one 360-degree video to another 360-degree video but the user is still limited to being in a fixed position at the center of one or the other 360-degree video, thus still encountering the disconnect between user movement in the real world and apparent movement in the VR environment.

In the present approach, the VR environment is treated as a virtual projection screen, i.e., a physical element that the user can move within. The virtual screen is treated as though it is a room planetarium in a small sphere of, for example, a diameter between 2 and 20 meters. A platform having a diameter of, for example, 6 feet upon which the VR user can move, can provide for a more comfortable and immersive 360-degree experience, even without additional features, and can help to reduce the discomfort that VR users often suffer in 360-degree environments.

Figure 10:
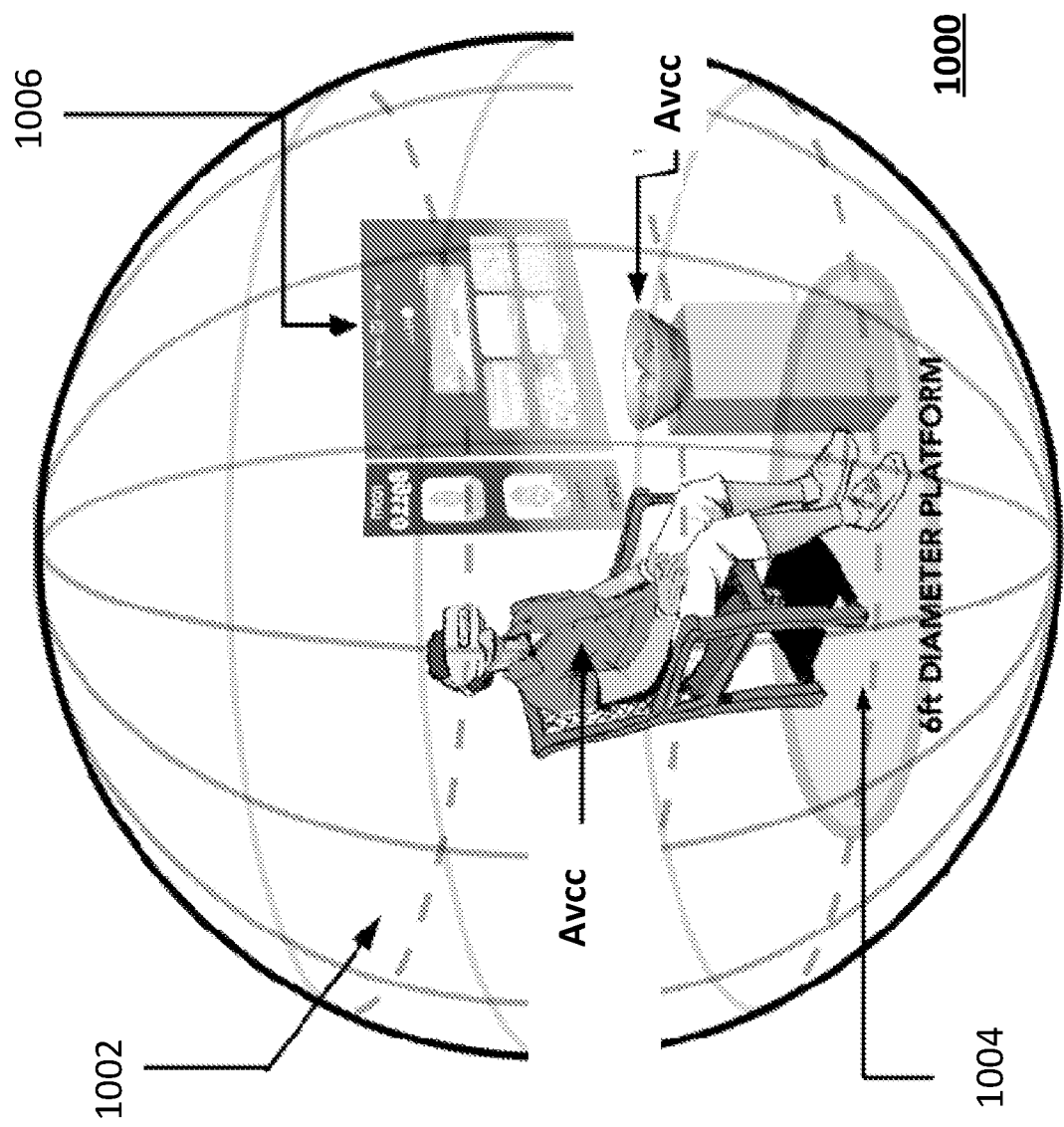
FIG. 10 is a diagram illustrating how a virtual reality environment may be configured for a virtual reality user to experience six degrees of freedom of movement in the virtual reality environment according to one embodiment of the present approach.

FIG. 10 is a diagram illustrating how a VR system 1000 can produce an environment configured to allow a VR user to experience 6DOF of movement in the VR environment according to one embodiment of the present approach.

A user wears a HMD that, as above, has a magnetic tracker. As is known in the art, information from the magnetic tracker allows the VR system to determine the physical position and orientation of the HMD, and thus the VR user's head. Upon entering the VR environment, the VR system determines the initial position and orientation of the HMD.

The VR environment is constructed as a projection on a virtual, spherical projection screen 1002 of a predetermined diameter. In one embodiment, it is expected that using a virtual projection screen with an apparent diameter of 2 to 20 meters will work, with an apparent diameter of 6 to 7 meters being optimal. The VR user may be given a "true ground," i.e., a physical platform 1004 that is, e.g., approximately 6 feet in diameter to allow the VR user to physically move while immersed in the VR environment.

The HMD displays video of a portion of the VR environment within a predetermined field of view that is comparable to the field of view that a user would see in the real world. The VR user will typically first see a particular portion of the VR environment that may also include, for example, a user interface 1006 containing menus or other means of selecting actions and applications, and any windows containing video of guest users as discussed above.

The VR system associates the user's initial view with the initial physical position and orientation of the HMD. The VR user may also see and, in some embodiments, be able to manipulate, virtual objects. Each virtual object has an associated apparent position, distance and size.

From the magnetic tracker in the HMD, the VR system determines when the HMD, and thus the user, moves, either rotationally or translationally. As is known in the prior art, excluding the windows of video from guest users as above, when the VR system determines that the VR user is moving rotationally, so that the VR user is looking in a different direction in the VR environment, the VR system will cause the HMD to display video of the appropriate portion of the VR environment.

In some embodiments of the present approach, the user interface and any virtual objects that were initially displayed to the VR user are not locked to the VR user's field of view, but are instead locked to the spherical projection screen so that, if the VR user turns away from the user interface or a virtual object, the user interface or virtual object will no longer be in the VR user's field of view. In such a case, the VR user must rotate back to their initial position to see those items. In some embodiments, any windows containing video from guest users may be locked into the VR user's field of view if desired, or may remain near the user interface, although in the latter case the effect of real-time communication may be diminished.

Alternatively, in some embodiments, the VR user can issue a command that immediately "recenters" the VR user, i.e., returns them to their initial view, so that the user interface is again available without the VR user having to rotate to see it. This prevents the VR user from being "lost" in the VR environment and unable to access the user interface. In such a case, the current position and orientation of the HMD may become associated with the initial view, replacing the original position and orientation of the HMD when the user entered the VR environment.

In the present approach, when the VR system determines that the VR user has moved translationally, the VR system adjusts the apparent position, distance and size of any virtual objects in the VR user's field of view. If the virtual object is "close enough" to the VR user in the VR environment, this will make them appear closer or more distant if the VR user has moved toward or away from them, or move them to the left and right if the VR user has moved in a transverse direction. Objects that are sufficiently distant will not be affected.

Figure 11:
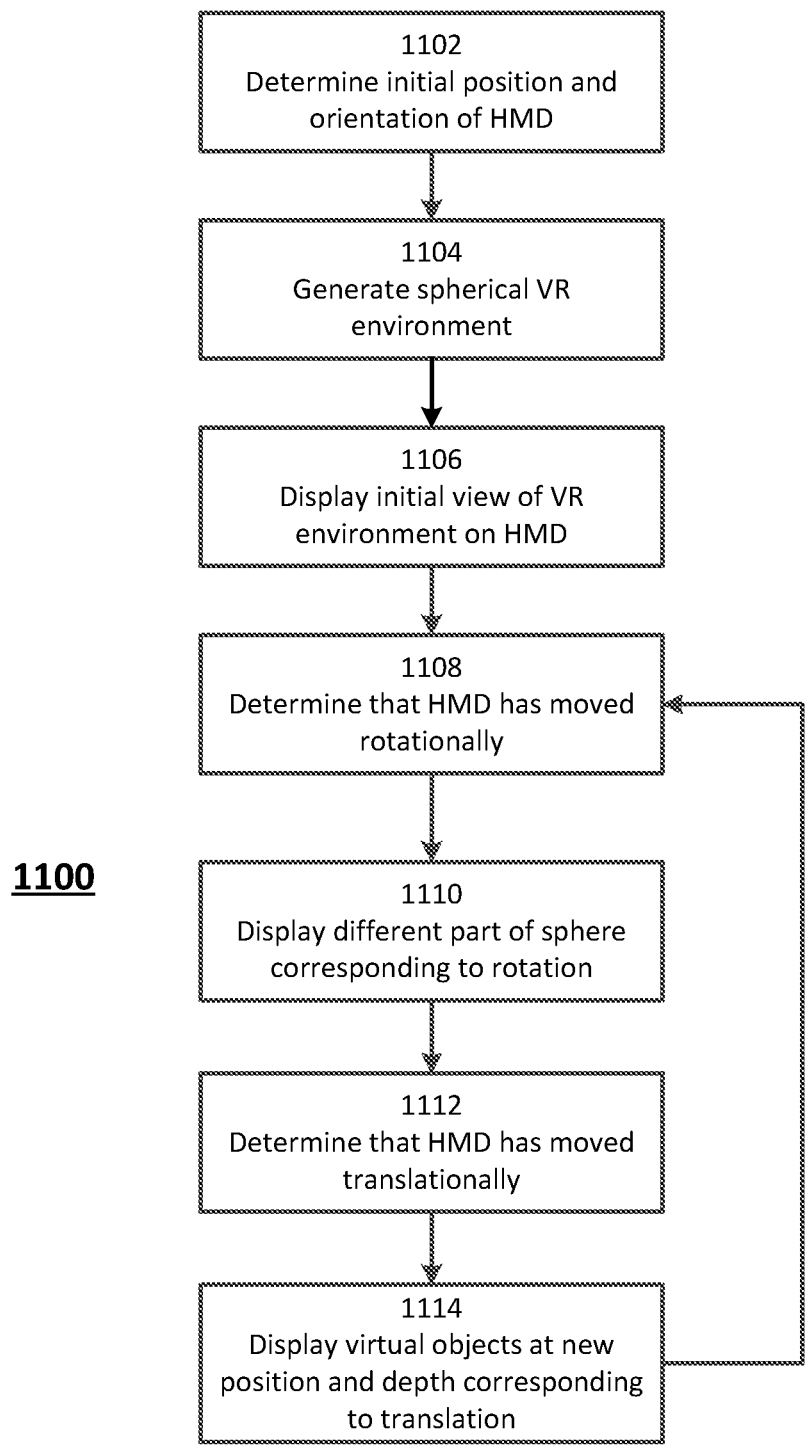
FIG. 11 is a flowchart of a method of providing a virtual reality user a virtual reality environment that supports six degrees of freedom of movement according to one embodiment of the present approach.

FIG. 11 is a flowchart of a method 1100 of providing a virtual reality user a virtual reality environment supporting six degrees of freedom of movement according to one embodiment of the present approach.

At step 1102, with a HMD placed on a VR user's head, the VR system determines the initial position and orientation of the HMD from a magnetic tracker in the HMD.

At step 1104, the VR system generates a spherical VR environment, using a virtual spherical projection screen as described above.

At step 1106, an initial view of the VR environment is displayed on the HMD. As above, the field of view on the HMD will be comparable to what the VR user would see in the real world, with an initial view that typically includes at least a user interface and any windows containing guest user video.

As is known in the art, the VR system continues to check the position and orientation of the HMD and, when there is movement of the HMD, determines how the HMD has changed its position and/or orientation, i.e., whether the movement of the HMD, and thus the VR user's head, is rotational and/or translational. At step 1108, the VR system determines from the magnetic tracker in the HMD that the VR user has moved rotationally. In response, at step 1110, the VR system displays on the HMD a different portion of the spherical environment that corresponds to the rotation.

At step 1112, the VR system determines that the VR user has moved translationally and in response, at step 1114, the VR system adjusts the apparent position, distance and size of any virtual objects in the field of view presented on the HMD to correlate with the HMD's new position and orientation. It will be appreciated that a VR user may change position both rotationally and translationally at the same time, and thus steps 1108 and 1112 may occur simultaneously or essentially so, and steps 1110 and 1114 may then occur simultaneously or essentially so, so that display to the VR user of the virtual environment changes in both ways at the same time, thus simulating what the VR user would see in the real world from a movement that is both rotational and translational.

The process then returns to step 1108 and the VR system continues to determine whether the VR user has moved from the last determined position and orientation. Further, as stated above, one of skill in the art will appreciate that there are other ways of determining the position and orientation of a HMD of a user, which can be used with this approach.

Figure 12:
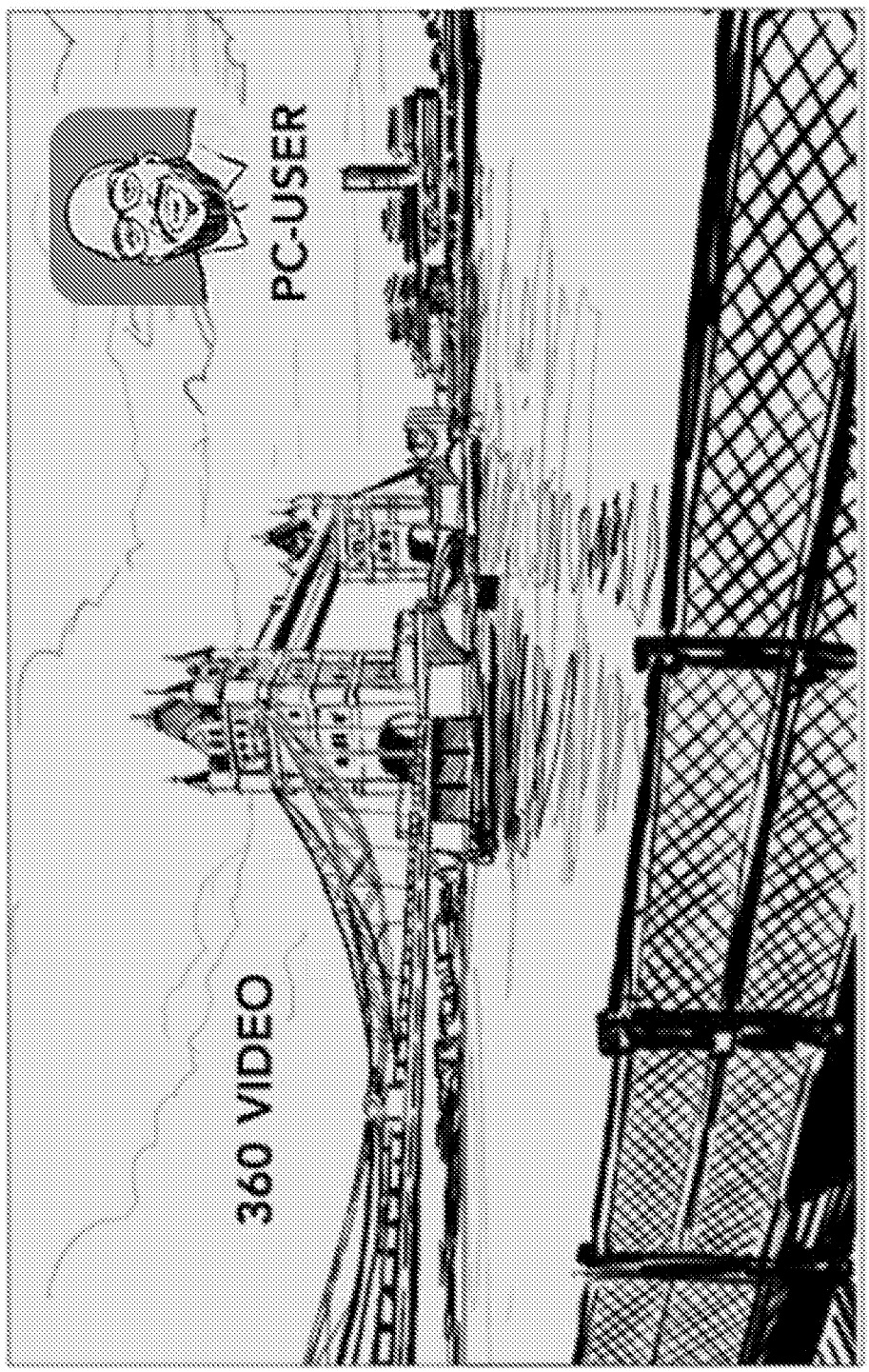
FIG. 12 is an illustration of a virtual reality user's field of view in a full presence immersive video according to one embodiment of the present approach.

FIG. 12 is an illustration of a VR user's field of view 1200 in a full presence immersive video according one embodiment of the present approach. The VR user cannot see the entire VR environment (here a site in London) at once, but rather only that portion of the VR environment that is within a field of view in the direction in which the user's head is turned is displayed on the HMD (here a view of the Tower Bridge). In this illustration, the VR user sees a seamless integration of layered interactive elements, with closer objects, such as the fence 1202, appearing closer as the VR user moves toward them, and more distant objects remaining in the background, such as the Tower Bridge, and the London skyline in the distance.

A window in the frame displayed to the VR user in FIG. 12 contains the current video feed from the camera in a computing device of a guest user (labeled "PC-User"), and the VR user and guest user can talk to each other in real time as described above. This ability to see the guest user as he appears on camera, rather than as a cartoon avatar as in the prior art, reduces or eliminates the uncanny valley effect and facilitates real-time two-way communication between the VR user and the guest user.

In some embodiments, the window containing the guest user's video feed may also be treated as a close 3D object, and thus allow the VR user to move closer and see a larger image of the guest user, just as the fence in FIG. 12 may be approached by the VR user, while in other embodiments the size of the window showing the guest user is fixed. In some embodiments the window showing the guest user remains in the frame seen by the VR user at all times, while in other embodiments the window may be located at a fixed position in the VR environment and thus at times will be out of the VR user's field of vision. In still other embodiments, the guest user may choose a video other than that being captured by the camera in the guest user's computing device and cause it to be displayed in the window in the VR environment.

The real-time two-way communication that is possible under the present approach can be useful in a wide variety of applications. One such application is shown in FIGS. 13 to 16, which illustrate various screens that might be displayed with respect to a VR session between a therapist, acting as a guest user, and a patient, acting as a VR user, according to the current approach.

Figure 13:
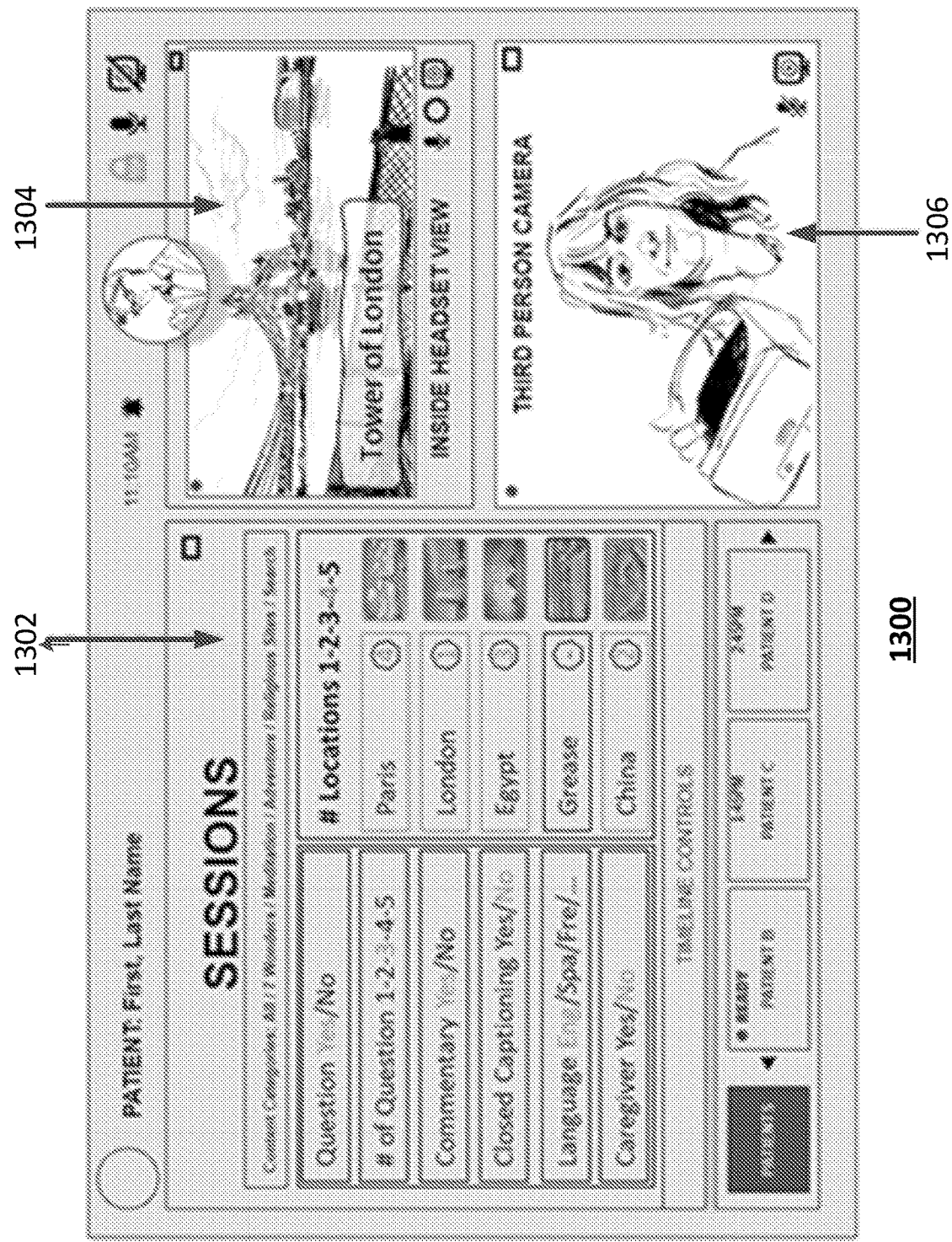
FIG. 13 shows a display that might be shown to a therapist, operating as a guest user, when a patient, operating as a virtual reality user, is preparing to begin a virtual reality therapy session in one embodiment of the present approach.

FIG. 13 shows a screen 1300 that might be displayed to a therapist when a patient is preparing to begin the VR therapy session. Screen 1300 contains a "dashboard" 1302 from which the therapist is able to select and control the content that is to be presented to the patient. Screen 1300 also contains a first window 1304 that displays the VR environment selected by the therapist to be displayed to the patient as it appears in a HMD, and a second window 1306 that shows a video feed of the patient from a camera at the patient's location. Here the patient is seen in window 1306 preparing to don the HMD.

Figure 14:
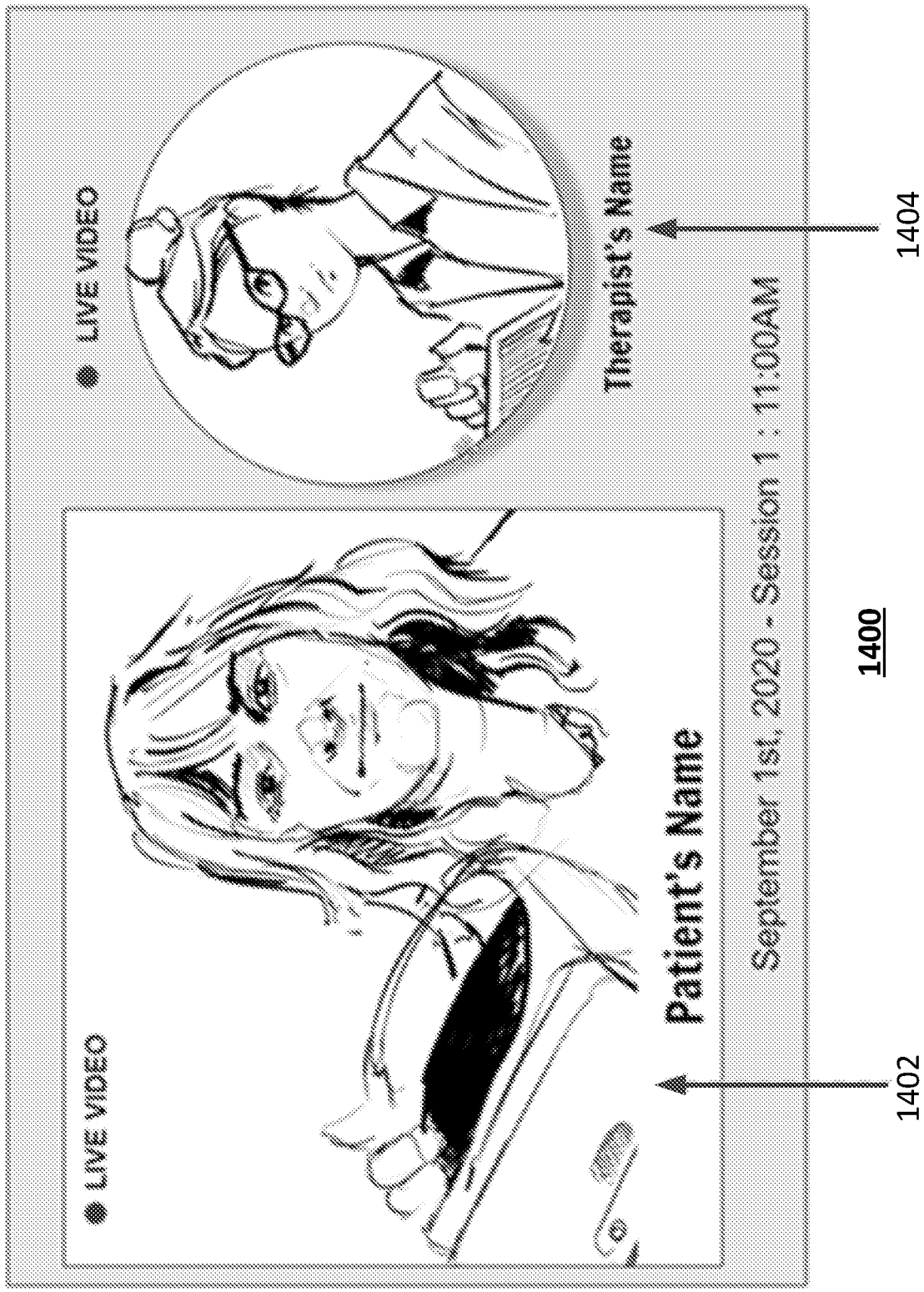
FIG. 14 shows a display that might be shown to a therapy patient, operating as a virtual reality user, when the patient is preparing to begin a virtual reality therapy session in one embodiment of the present approach.

FIG. 14 shows a screen 1400 that might be displayed to the VR user patient on a computing device when the patient is preparing to begin the VR therapy session, before the patient has entered a VR environment. The patient might see, for example, a first window 1402 with a video feed of the patient themself and a second window 1404 with a video feed of the guest user therapist. In window 1402, as in window 1306 in FIG. 13, the patient is seen preparing to don the HMD and enter a VR environment.

Figure 15:
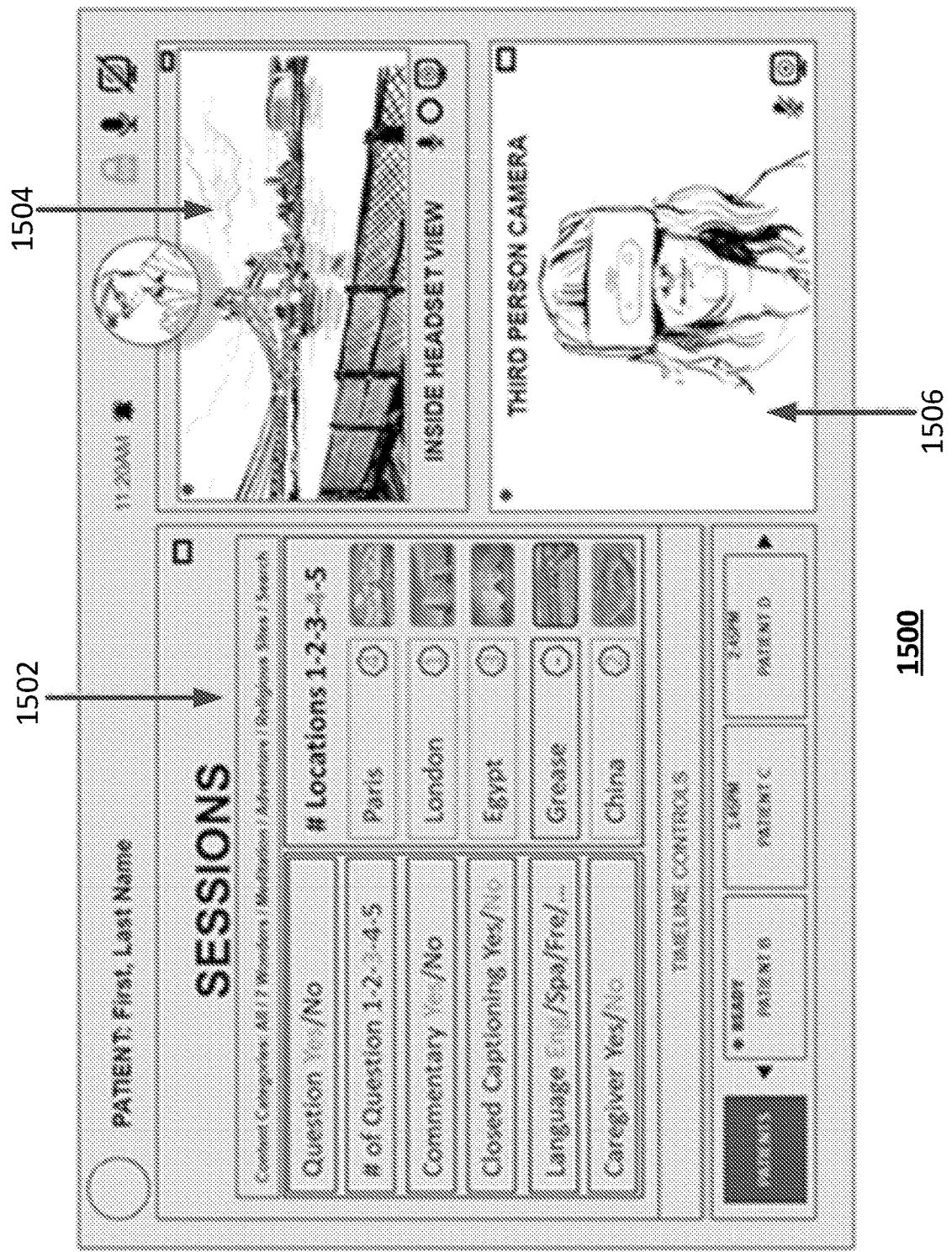
FIG. 15 shows a display that might be shown to a therapist, operating as a guest user, after a patient, operating as a virtual reality user, has donned a HMD and entered a virtual reality therapy session in one embodiment of the present approach.

FIG. 15 shows a screen 1500 that might be displayed to a guest user therapist after the VR user patient has donned the HMD and entered the VR therapy session. Screen 1500 again contains the dashboard 1502 which the therapist uses to control the content presented to the patient; this will be the same as dashboard 1302 in FIG. 13 unless the therapist has made changes since the user entered the VR environment. Screen 1500 again contains a first window 1504 that shows a portion of the VR environment displayed to the patient as it appears in a HMD as described above, and a second window 1506 that again shows a video feed of the patient from a camera at the patient's location, now wearing the HMD.

FIG. 16 shows the VR environment as displayed to and viewed by the VR user patient in the HMD. In this example, the VR environment is the same as that shown in FIG. 12, except that the patient sees the therapist in a window as the guest user. As described above, the patient can change their position and orientation in the VR environment and view the VR environment in different directions by moving their head rotationally, and can move translationally to approach, for example, the fence in the VR environment.

Using the present approach as described above, the guest user therapist is able to see what the VR user patient sees in the VR environment and the VR user patient is able to see and talk with the guest user therapist in real time. The virtual location (again here London) can be selected to improve the therapist's ability to provide instruction and emotional support; for example, a peaceful location, or one that has particular meaning to the patient, can be selected, thus potentially enhancing the effectiveness of the therapy session.

Various types of therapy can benefit from this approach, including psychotherapy, or drug and alcohol treatment (group sessions are possible with multiple users as described above). In some embodiments, a VR user may have, in addition to a HMD, magnetic trackers attached to their arms, legs, hands and/or feet, so that they can see the physical movements of their extremities in the VR environment (such as seen in FIG. 1, in which virtual hands of VR-User 2 are displayed) while a physical therapist guest user views the VR user's field of vision. This can greatly enhance the ability of the physical therapist to guide the VR user through physical therapy and/or occupational therapy remotely. While current telehealth applications, which rely on current videoconference techniques, may allow a therapist to see what a patient is doing, using the present approach the therapist can guide and direct the user's movements while also seeing what the VR user patient is actually seeing.

Other potential applications in the healthcare field include reducing the isolation and loneliness of patients in the hospital or residents in a senior care facility who cannot physically receive visitors due to either visitation restrictions or distance. Such VR user patients can virtually visit any location in the world and be virtually accompanied by guest user family members. The present approach may also be useful in allowing VR user patients undergoing pain therapy to be distracted by virtually visiting a location that they cannot physically visit, or simply by connecting with guest user family members or friends.

The present approach also has many potential applications in the educational and training fields. Instructors may supervise video training sessions with students in either group or one-to-one settings. A sports coach can provide and control video content displayed to athletes to simulate situations that arise in competition and provide instruction without requiring the athletes to leave the VR environment. In these and other cases the ability of a VR user receiving instruction in a VR environment to see the guest user teacher or trainer's facial expressions and hear their voice can help provide more effective instruction and emotional support.

Finally, in the case of patients with disabilities that prevent them from controlling or directing content, such as paraplegics, a guest user can perform these functions for a VR user from a local or remote location.

While the description herein has been provided with respect to VR systems and environments, one of skill in the art will appreciate that the same approaches may be used with augmented reality (AR) systems and mixed reality (MR) systems. In such cases, in a further embodiment, an additional camera can be used to capture the AR or MR user's view of the real world, and that view overlaid with the virtual elements provided by the AR or MR system.

The disclosed system and method has been explained above with reference to several embodiments. Other embodiments will be apparent to those skilled in the art in light of this disclosure. Certain aspects of the described method and apparatus may readily be implemented using configurations or steps other than those described in the embodiments above, or in conjunction with elements other than or in addition to those described above. It will also be apparent that in some instances the order of steps described herein may be altered without changing the result of performance of all of the described steps.

There may be a single processor, or multiple processors performing different functions of the methods described herein. The connection application may be located locally to the VR system or the guest user computing device if those devices are in a single location, or may reside in a server and be accessed over a network such as the internet if they are remote from each other. One of skill in the art will appreciate how to determine which and how many processors will be appropriate for a specific intended application, and where in a given system they might be located.

It should also be appreciated that the described method and apparatus can be implemented in numerous ways, including as a process, an apparatus, or a system. The methods described herein may be implemented by program instructions for instructing a processor to perform such methods, and such instructions recorded on a non-transitory computer readable storage medium such as a hard disk drive, floppy disk, optical disc such as a compact disc (CD) or digital versatile disc (DVD), flash memory, etc. It may be possible to incorporate the described methods into hard-wired logic if desired. It should be noted that the order of the steps of the methods described herein may be altered and still be within the scope of the disclosure.

These and other variations upon the embodiments are intended to be covered by the present disclosure, which is limited only by the appended claims.

What is claimed is:

1. A method of providing real-time, two-way communication between a virtual reality user, viewing on a virtual reality display device a displayed sequence of video frames comprising the virtual reality user's field of view of a virtual reality environment, and a guest user operating a computing device having a camera and microphone, comprising:
    creating, by a processor, a connection between the virtual reality display device and the computing device of the guest user;
    capturing, by the processor, the sequence of video frames displayed to the virtual reality user on the virtual reality display device;
    generating, by a microphone, an audio signal from the virtual reality user;
    obtaining, by the processor, permission from the virtual reality user before creating a connection between the virtual reality display device and the computing device of the guest user;
    sending, by the processor, the captured sequence of video frames displayed to the virtual reality user and the generated audio signal from the virtual reality user to the computing device of the guest user;
    displaying, by the computing device of the guest user, the captured sequence of video frames;
    playing, by the computing device of the guest user, the generated audio signal from the virtual reality user;
    capturing, by the camera of the computing device of the guest user, a video stream of the guest user;
    generating, by the microphone of the computing device of the guest user, an audio signal from the guest user;
    sending, by the computing device of the guest user, the captured video stream of the guest user and the generated audio signal from the guest user to the processor;
    displaying, by the processor, the captured video stream of the guest user in a window in the virtual reality environment; and
    playing, by the processor, the generated audio signal from the guest user.

2. The method of claim 1 wherein the virtual reality display device is a head-mounted display.

3. The method of claim 1 wherein the computing device of the guest user is a laptop computer, desktop computer, smartphone or computer tablet.

4. The method of claim 1, further comprising authenticating the computing device of the guest user before obtaining permission from the virtual reality user.

5. A method of providing real-time, two-way communication between a virtual reality user, viewing on a virtual reality display device a displayed sequence of video frames comprising the virtual reality user's field of view of a virtual reality environment, and a guest user operating a computing device having a camera and microphone, comprising:
    obtaining, by a processor, permission from the guest user before creating a connection between the virtual reality display device and the computing device of the guest user;
    creating, by the processor, the connection between the virtual reality display device and the computing device of the guest user;
    capturing, by the processor, the sequence of video frames displayed to the virtual reality user on the virtual reality display device;
    generating, by a microphone, an audio signal from the virtual reality user;
    sending, by the processor, the captured sequence of video frames displayed to the virtual reality user and the generated audio signal from the virtual reality user to the computing device of the guest user;
    displaying, by the computing device of the guest user, the captured sequence of video frames;
    playing, by the computing device of the guest user, the generated audio signal from the virtual reality user;
    capturing, by the camera of the computing device of the guest user, a video stream of the guest user;
    generating, by the microphone of the computing device of the guest user, an audio signal from the guest user;

sending, by the computing device of the guest user, the captured video stream of the guest user and the generated audio signal from the guest user to the processor;

displaying, by the processor, the captured video stream of the guest user in a window in the virtual reality environment; and playing, by the processor, the generated audio signal from the guest user.

6. A method of providing real-time, two-way communication between a virtual reality user, viewing on a virtual reality display device a displayed sequence of video frames comprising the virtual reality user's field of view of a virtual reality environment, and a guest user operating a computing device having a camera and microphone, comprising:

creating, by a processor, a connection between the virtual reality display device and the computing device of the guest user;

capturing, by the processor, the sequence of video frames displayed to the virtual reality user on the virtual reality display device;

generating, by a microphone, an audio signal from the virtual reality user;

sending, by the processor, the captured sequence of video frames displayed to the virtual reality user and the generated audio signal from the virtual reality user to the computing device of the guest user;

displaying, by the computing device of the guest user, the captured sequence of video frames;

playing, by the computing device of the guest user, the generated audio signal from the virtual reality user;

capturing, by the camera of the computing device of the guest user, a video stream of the guest user;

generating, by the microphone of the computing device of the guest user, an audio signal from the guest user;

sending, by the computing device of the guest user, the captured video stream of the guest user and the generated audio signal from the guest user to the processor;

displaying, by the processor, the captured video stream of the guest user in a window in the virtual reality environment;

playing, by the processor, the generated audio signal from the guest user;

sending, by the computing device of the guest user, a second video stream from the guest user computing device that is not the captured video stream of the guest user and a second audio signal from the guest user computing device to the processor; and displaying, by the processor, the second video stream from the guest user computing device in a window in the virtual reality environment and playing the second audio signal from the guest user computing device.

7. A system for providing real-time two-way communication between a virtual reality user, and a guest user operating a computing device containing a camera and microphone, comprising:

a virtual reality display device configured to display a sequence of video frames comprising the virtual reality user's field of view of a virtual reality environment;

a microphone configured to generate a first audio signal from the virtual reality user;

a processor configured to:
obtain permission from the virtual reality user before creating a connection between the virtual reality display device and the computing device of the guest user;

create the connection between the virtual reality display device and the computing device of the guest user;

capture the sequence of video frames displayed to the virtual reality user on the virtual reality display device;

send the captured sequence of frames displayed to the virtual reality user and the first audio signal to the computing device of the guest user;

receive a video stream and a second audio signal from the computing device of the guest user;

display the video stream from the computing device of the guest user in a window in the virtual reality environment; and a transducer configured to play the second audio signal.

8. The system of claim 7 wherein the virtual reality display device is a head-mounted display.

9. The system of claim 7 wherein the computing device of the guest user is a laptop computer, desktop computer, smartphone or computer tablet.

10. The system of claim 7, wherein the processor is further configured to authenticate the computing device of the guest user before obtaining permission from the virtual reality user.

11. A system for providing real-time two-way communication between a virtual reality user, and a guest user operating a computing device containing a camera and microphone, comprising:

a virtual reality display device configured to display a sequence of video frames comprising the virtual reality user's field of view of a virtual reality environment;

a microphone configured to generate a first audio signal from the virtual reality user;

a processor configured to:
obtain permission from the guest user before creating a connection between the virtual reality display device and the computing device of the guest user;

create the connection between the virtual reality display device and the computing device of the guest user;

capture the sequence of video frames displayed to the virtual reality user on the virtual reality display device;

send the captured sequence of frames displayed to the virtual reality user and the first audio signal to the computing device of the guest user;

receive a video stream and a second audio signal from the computing device of the guest user;

display the video stream from the computing device of the guest user in a window in the virtual reality environment; and a transducer configured to play the second audio signal.

12. A system for providing real-time two-way communication between a virtual reality user, and a guest user operating a computing device containing a camera and microphone, comprising:

a virtual reality display device configured to display a sequence of video frames comprising the virtual reality user's field of view of a virtual reality environment;

a microphone configured to generate a first audio signal from the virtual reality user;

a processor is further configured to:
create the connection between the virtual reality display device and the computing device of the guest user;

capture the sequence of video frames displayed to the virtual reality user on the virtual reality display device;

send the captured sequence of frames displayed to the virtual reality user and the first audio signal to the computing device of the guest user;

receive a video stream and a second audio signal from the computing device of the guest user;
display the video stream from the computing device of the guest user in a window in the virtual reality environment;
receive a second video stream and a third audio signal from the guest user computing;
display the second video stream from the guest user computing device in a window in the virtual reality environment and play the third audio signal; and
a transducer configured to play the second audio signal.

13. A non-transitory computer readable storage medium having embodied thereon instructions for causing a computing device to execute a method for providing real-time, two-way communication between a virtual reality user, viewing on a virtual reality display device a displayed sequence of video frames comprising the virtual reality user's field of view of a virtual reality environment, and a guest user operating a computing device having a camera and microphone, the method comprising:

obtaining, by a processor, permission from the virtual reality user before creating a connection between the virtual reality display device and the computing device of the guest user;
creating, by the processor, the connection between the virtual reality display device and the computing device of the guest user;
capturing, by the processor, the sequence of video frames displayed to the virtual reality user on the virtual reality display device;
generating, by a microphone, an audio signal from the virtual reality user;
sending, by the processor, the captured sequence of video frames displayed to the virtual reality user and the generated audio signal from the virtual reality user to the computing device of the guest user;
displaying, by the computing device of the guest user, the captured sequence of video frames;
playing, by the computing device of the guest user, the generated audio signal from the virtual reality user;
capturing, by the camera of the computing device of the guest user, a video stream of the guest user;
generating, by the microphone of the computing device of the guest user, an audio signal from the guest user;
sending, by the computing device of the guest user, the captured video stream of the guest user and the generated audio signal from the guest user to the processor;
displaying, by the processor, the captured video stream of the guest user in a window in the virtual reality environment; and
playing, by the processor, the generated audio signal from the guest user.

14. A non-transitory computer readable storage medium having embodied thereon instructions for causing a computing device to execute a method for providing real-time, two-way communication between a virtual reality user, viewing on a virtual reality display device a displayed sequence of video frames comprising the virtual reality user's field of view of a virtual reality environment, and a guest user operating a computing device having a camera and microphone, the method comprising:

authenticating, by a processor, the computing device of the guest user before obtaining permission from the virtual reality user;
creating, by the processor, a connection between the virtual reality display device and the computing device of the guest user;
capturing, by the processor, the sequence of video frames displayed to the virtual reality user on the virtual reality display device;
generating, by a microphone, an audio signal from the virtual reality user;
sending, by the processor, the captured sequence of video frames displayed to the virtual reality user and the generated audio signal from the virtual reality user to the computing device of the guest user;
displaying, by the computing device of the guest user, the captured sequence of video frames;
playing, by the computing device of the guest user, the generated audio signal from the virtual reality user;
capturing, by the camera of the computing device of the guest user, a video stream of the guest user;
generating, by the microphone of the computing device of the guest user, an audio signal from the guest user;
sending, by the computing device of the guest user, the captured video stream of the guest user and the generated audio signal from the guest user to the processor;
displaying, by the processor, the captured video stream of the guest user in a window in the virtual reality environment; and
playing, by the processor, the generated audio signal from the guest user.

15. A non-transitory computer readable storage medium having embodied thereon instructions for causing a computing device to execute a method for providing real-time, two-way communication between a virtual reality user, viewing on a virtual reality display device a displayed sequence of video frames comprising the virtual reality user's field of view of a virtual reality environment, and a guest user operating a computing device having a camera and microphone, the method comprising:

obtaining, by a processor, permission from the guest user before creating a connection between the virtual reality display device and the computing device of the guest user;
creating, by the processor, the connection between the virtual reality display device and the computing device of the guest user;
capturing, by the processor, the sequence of video frames displayed to the virtual reality user on the virtual reality display device;
generating, by a microphone, an audio signal from the virtual reality user;
sending, by the processor, the captured sequence of video frames displayed to the virtual reality user and the generated audio signal from the virtual reality user to the computing device of the guest user;
displaying, by the computing device of the guest user, the captured sequence of video frames;
playing, by the computing device of the guest user, the generated audio signal from the virtual reality user;
capturing, by the camera of the computing device of the guest user, a video stream of the guest user;
generating, by the microphone of the computing device of the guest user, an audio signal from the guest user;
sending, by the computing device of the guest user, the captured video stream of the guest user and the generated audio signal from the guest user to the processor;
displaying, by the processor, the captured video stream of the guest user in a window in the virtual reality environment; and playing, by the processor, the generated audio signal from the guest user.

* * * * *